United States Patent
Peumans et al.

(10) Patent No.: US 11,241,687 B2
(45) Date of Patent: Feb. 8, 2022

(54) COMPACT GLASS-BASED FLUID ANALYSIS DEVICE AND METHOD TO FABRICATE

(71) Applicant: IMEC VZW, Leuven (BE)

(72) Inventors: Peter Peumans, Herfelingen (BE); Liesbet Lagae, Leuven (BE); Paolo Fiorini, Brussels (BE)

(73) Assignee: IMEC VZW, Leuven (BE)

( * ) Notice: Subject to any disclaimer, the term of this patent is extended or adjusted under 35 U.S.C. 154(b) by 485 days.

(21) Appl. No.: 15/529,396

(22) PCT Filed: Nov. 26, 2015

(86) PCT No.: PCT/EP2015/077855
§ 371 (c)(1),
(2) Date: May 24, 2017

(87) PCT Pub. No.: WO2016/083550
PCT Pub. Date: Jun. 2, 2016

(65) Prior Publication Data
US 2017/0326546 A1  Nov. 16, 2017

(30) Foreign Application Priority Data
Nov. 26, 2014  (EP) ................. EP14194864

(51) Int. Cl.
*B01L 3/00* (2006.01)
*A61K 9/00* (2006.01)
*B01L 9/00* (2006.01)

(52) U.S. Cl.
CPC ...... *B01L 3/502707* (2013.01); *A61K 9/0014* (2013.01); *B01L 3/5027* (2013.01);
(Continued)

(58) Field of Classification Search
CPC .......... B01L 3/502707; B01L 3/50273; B01L 3/50857; B01L 3/565; B01L 9/527;
(Continued)

(56) References Cited

U.S. PATENT DOCUMENTS 7,615,762 B2 * 11/2009 Satyanarayana ........ B03C 5/005
250/461.2
8,639,074 B2 * 1/2014 Tang ................... G02B 6/12007
356/73.1
(Continued)

FOREIGN PATENT DOCUMENTS

WO  2012/017185 A1  2/2012

OTHER PUBLICATIONS

Minas et al. "Highly Selective Optical Detection in a Lab-on-a-Chip for Biological Fluids Analysis" Sensors and Materials, vol. 14, No. 2 (2002) 077-089 (Year: 2002).*
(Continued)

*Primary Examiner* — Benjamin R Whatley
*Assistant Examiner* — Quocan B Vo
(74) *Attorney, Agent, or Firm* — McDonnell Boehnen Hulbert & Berghoff LLP

(57) ABSTRACT

The present disclosure relates to devices and methods for analyzing a fluid sample. An example device comprises a fluidic substrate comprising a micro-fluidic component embedded therein, for propagating a fluid sample; a needle or inlet for providing the fluid sample which is fluidically connected to the micro-fluidic component; a lid attached to the fluidic substrate thereby at least partly covering the fluidic substrate and at least partly closing the micro-fluidic component; wherein the fluidic substrate is a glass fluidic substrate and wherein the lid is a microchip. The present disclosure also relates to a method for fabricating a fluid analysis device. The method comprises providing a fluidic
(Continued)

substrate; providing a lid; attaching the lid to the fluidic substrate to close the fluidic substrate at least partly.

20 Claims, 15 Drawing Sheets

(52) U.S. Cl.
CPC ....... B01L 3/50273 (2013.01); B01L 3/50857 (2013.01); B01L 3/565 (2013.01); B01L 9/527 (2013.01); B01L 2200/10 (2013.01); B01L 2300/0645 (2013.01)

(58) Field of Classification Search
CPC ......... B01L 2300/0645; B01L 2200/10; B01L 3/5027; A61K 9/0014
See application file for complete search history.

(56) References Cited

U.S. PATENT DOCUMENTS

| | | | | |
|---|---|---|---|---|
| 2002/0037499 | A1* | 3/2002 | Quake | B01L 3/02 435/6.13 |
| 2002/0042125 | A1* | 4/2002 | Petersen | B01L 3/502715 435/287.2 |
| 2002/0058273 | A1* | 5/2002 | Shipwash | B01L 3/502753 435/287.2 |
| 2002/0142471 | A1* | 10/2002 | Handique | B01L 3/5027 435/6.19 |
| 2003/0019522 | A1* | 1/2003 | Parunak | F15C 3/002 137/251.1 |
| 2003/0083685 | A1* | 5/2003 | Freeman | A61B 5/15178 606/181 |
| 2004/0005582 | A1* | 1/2004 | Shipwash | B01L 3/5027 435/6.19 |
| 2004/0053290 | A1* | 3/2004 | Terbrueggen | B01L 3/50273 435/6.11 |
| 2004/0132059 | A1* | 7/2004 | Scurati | B01L 3/502715 435/6.18 |
| 2004/0253821 | A1* | 12/2004 | Howitz | B01L 3/502707 438/689 |
| 2005/0171480 | A1* | 8/2005 | Mukerjee | A61M 37/0015 604/173 |
| 2009/0169427 | A1 | 7/2009 | Supriya et al. | |
| 2009/0269767 | A1* | 10/2009 | Soderlund | B01L 3/50273 435/6.11 |
| 2010/0159590 | A1* | 6/2010 | Alley | C12M 23/12 435/374 |
| 2010/0297640 | A1* | 11/2010 | Kumar | B01L 7/52 435/6.11 |
| 2014/0061049 | A1* | 3/2014 | Lo | G01N 27/44704 204/547 |
| 2015/0211048 | A1* | 7/2015 | Ramsey | C12Q 1/6823 506/12 |
| 2016/0066789 | A1* | 3/2016 | Rogers | A61N 1/05 604/20 |
| 2016/0367988 | A1* | 12/2016 | Azpiroz | G01N 27/44743 |

OTHER PUBLICATIONS

Roula et al., "A multispectral computer vision system for automatic grading of prostatic neoplasia," Proceedings IEEE International Symposium on Biomedical Imaging, Washington, Dc, USA, 2002, pp. 193-196 (Year: 2002).*
Kawai et al. "Fabrication of vertical and high-aspect-ratio glass microfluidic device by borosilicate glass molding to silicon structure" 14th International Conference on Miniaturized Systems for Chemistry and Life Sciences Oct. 3-7, 2010, Groningen, The Netherlands (Year: 2010).*
PCT International Search Report and Written Opinion, PCT International Application No. PCT/EP2015/077855, dated Feb. 23, 2016, 8 pages.
Tanaka, Hiroyuki et al., "Electrochemical Sensor With Dry Reagents Implemented in Lab-on-Chip for Single Nucleotide Polymorphism Detection", Japanese Journal of Applied Physics, No. 53, Apr. 17, 2014, pp. 1-5.

* cited by examiner

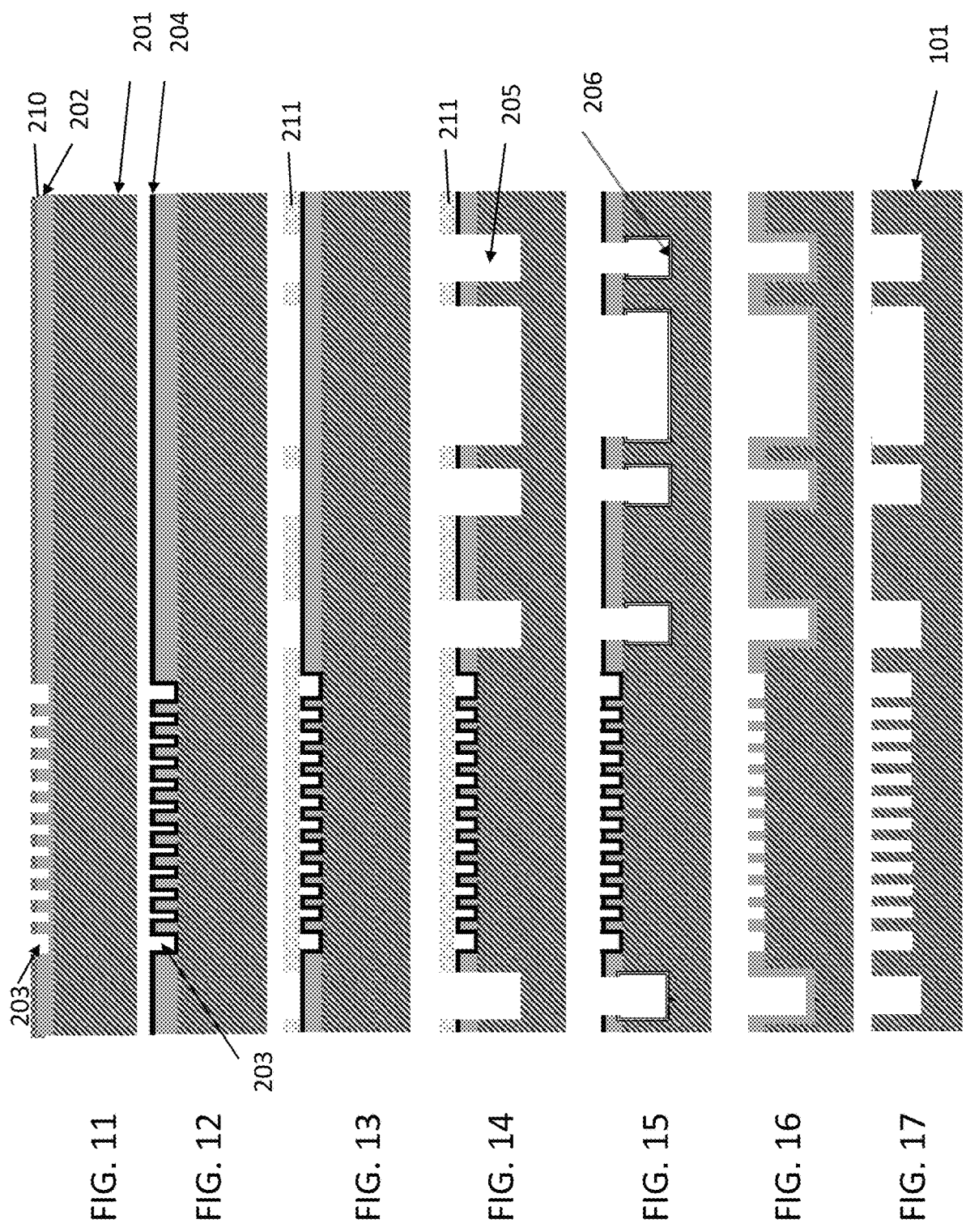

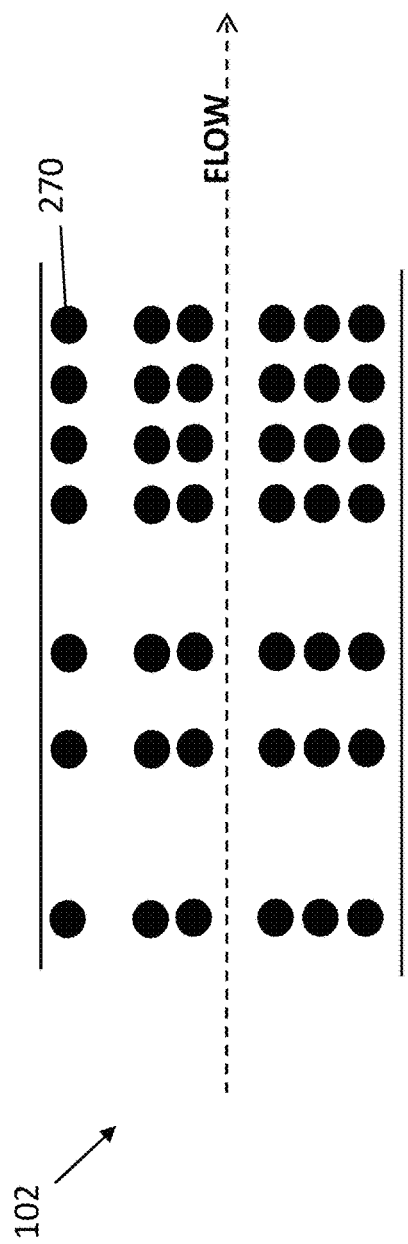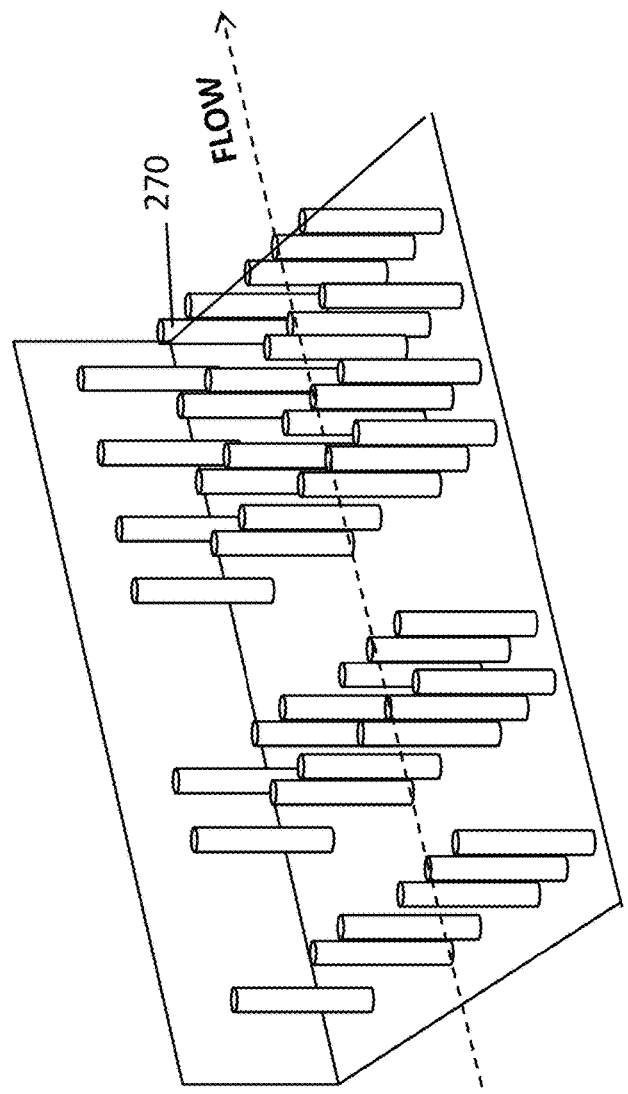

COMPACT GLASS-BASED FLUID ANALYSIS DEVICE AND METHOD TO FABRICATE

CROSS-REFERENCE TO RELATED APPLICATION

The present application is a national stage entry of PCT/EP2015/077855 filed Nov. 26, 2015, which claims priority to European Patent Application No. 14194864.6 filed Nov. 26, 2014, the contents of which are hereby incorporated by reference.

FIELD OF THE DISCLOSURE

The present disclosure relates to the field of biological analysis devices. In particular, the present disclosure is related to compact medical devices for the analysis of a fluid sample. More in particular, the present disclosure is related to fully integrated lab-on-a-chip devices for the analysis of fluid samples.

BACKGROUND

Currently, conventional point-of-care devices exist for the analysis of blood. A disadvantage of these devices is their size which depends on the different components needed to perform analysis of blood. In these devices, external pumps are part of the point of care instrument. In some devices, miniature scale pumps are used to propagate a sample through the fluidic channels of the device. The use of pumps increases the size and cost of the device which makes them less suitable for usage as a disposable device. Current disposable devices are typically inserted in expensive read-out instruments; with many non-disposable different electronic or optical components to read out the biochemical reactions taking place in the disposable. Another disadvantage of conventional point of care devices is their cost to fabricate.

Other conventional devices are lateral flow test strips. These test strips are usually fabricated from cellulose which does not allow a precise control of the flow of a fluid sample propagating through the test strips. This narrows the scope of application of these devices.

SUMMARY

The embodiments described herein provide devices for the analysis of a fluid sample. This is accomplished by a device according to the present disclosure, and a method for fabricating such device.

In a first aspect, the present disclosure relates to a device for analyzing a fluid sample. The device comprises: a fluidic substrate comprising: a micro-fluidic component embedded in the fluidic substrate configured to propagate a fluid sample through the micro-fluidic component; and a means for providing a fluid sample connected to the micro-fluidic component; a lid attached to the fluidic substrate at least partly covering the fluidic substrate and at least partly closing the micro-fluidic component. The lid is a microchip, e.g. a CMOS chip.

According to some embodiments, the fluidic substrate is a glass substrate.

The embodiments described herein allow for a low-cost, easy to use, disposable, compact device to be provided for the fully integrated analysis of a fluid sample.

The embodiments described herein allow for mass production technologies to be used to manufacture the device as the fluidic substrate is a glass substrate and the lid a microchip. The embodiments described herein improve the functionality, portability and manufacturability of compact disposable point of care devices.

The embodiments described herein allow for the glass to be used as a material for the fluidic substrate which is an inert material with advantages towards implementation of biochemical reactions.

As the fluidic substrate is a glass substrate and the lid is a microchip, it is an advantage that both and thus the device can be manufactured using mass production process technologies. As an additional advantage, cheap packaging techniques may be used to attach (e.g. bond) the glass substrate to the microchip. This reduces the total cost of the device and allows it to be used as a disposable device and produced in high volume.

According to some embodiments, the fluidic substrate is a glass silicon substrate.

According to some embodiments, the fluidic substrate is configured to propagate a fluid sample through the micro-fluidic component via capillary force.

According to some embodiments, the fluidic substrate comprises a vacuum compartment which is connectable to the micro-fluidic component and which is adapted for creating a suction force in the micro-fluidic component when the vacuum compartment is opened, thereby propagating a fluid sample through the micro-fluidic component.

The embodiments described herein allow for the device to not need additional active components (e.g. an active pump) to propagate a fluid sample through the device. Thus, the complexity of the device is reduced compared to conventional implementations, which reduces fabrication cost and power consumption. As the costs to fabricate are low, the device may be used as a disposable fluid analysis device.

According to some embodiments, at least a part of the lid is in direct contact with the fluid sample when the fluid sample is present in the device. According to some embodiments, the lid comprises a transistor layer, the transistor layer being electrically connected to at least one electrical component, the electrical component comprising or being at least one of the following: biosensing circuitry, biosensing circuitry for fluorescent detection, biosensing circuitry for lens-free detection of particles, electrodes for sensing purposes, electrodes for fluid manipulation purposes, circuitry for data communication purposes, circuitry for wireless data communication purposes, temperature sensors, heater electrodes for temperature control and fluid sensors and electrodes for fluidic viscosity control.

According to some embodiments, the means for providing a fluid sample is needle integrated in the fluidic substrate, fabricated from glass and comprising an inner fluidic channel connected to the micro-fluidic component. The needle is a protruding portion of the fluidic substrate and is positioned to penetrate skin tissue when pressed against the skin tissue.

The embodiments described herein allow for when the fluidic substrate and the needle are fabricated from a single piece of glass, the fabrication of the device is simplified, as separate additional steps to attach a needle to the fluidic substrate become obsolete. In addition, the strength of the glass allows the needle to be very sharp which eases the penetration of the needle in skin tissue of the user. Further, the strength of the glass allows the skin tissue to be firmly pressed against the needle allowing penetration of skin tissue without bending or breaking of the needle.

In some embodiments, the needle is sharp with a small outer diameter, possibly smaller than 200 µm, resulting in the penetration of the skin not causing any discomfort, or only limited discomfort, to the user.

According to alternative embodiments, the means for providing a fluid sample is a system comprising a portion having sharp objects. The portion can be actuated by the user towards the skin of the user. The sharp objects are positioned such that they puncture the skin when the portion is actuated. This way a blood sample from the user can be obtained. Further, the system comprises a fluidic channel adapted for sucking the obtained blood sample, e.g. via capillary force. The fluidic channel is in fluidic connection with the fluidic substrate such that the fluid sample can be provided to the fluidic substrate.

According to some embodiments, the fluidic substrate comprises a cut-out and the needle is positioned in the cut-out.

The embodiments described herein allow for the needle to be fabricated as a consequence of fabricating the cut-out. As a result, less material is wasted as only the material for the cut-out is wasted, excluding the material needed for the needle. In addition, the cut-out and needle can be fabricated using standard micromachining processing techniques.

According to some embodiments of, the fluidic substrate comprises a protection structure for protecting the needle, removably attached to the fluidic substrate.

According to some embodiments, the means for providing a fluid sample is an inlet. A sample drop may be inserted into the microfluidic component by means of: 1) capillary suction, for example generated by a capillary pump; or 2) a suction force created in the micro-fluidic component by a vacuum compartment which is opened when the fluid sample is provided. The microfluidic component may comprise different fluidic compartments, e.g. micro-fluidic channels, for instance for multi-omic analysis. The different microfluidic compartments can have same or different depths. The different microfluidic compartments may be separated by valves that may be actuated in any suitable way, for instance by fluidic forces or by electricity. Electrodes for actuation may be contained on the fluidic substrate or on the lid.

According to some embodiments, the fluidic substrate and/or the lid may further comprise at least one optical waveguide to allow optical excitation and sensing of the fluid sample when present in the device. The fluidic substrate and/or the lid may also comprise filters for rejecting optical excitation from emission to measure a fluorescent signal. The fluidic substrate and/or the lid may comprise filters, for instance multispectral filters for measuring fluorescent signals with multiple colors. The fluidic substrate and/or the lid may comprise an optical waveguide and/or a pinhole to irradiate the sample for performing lens-free microscopy.

According to some embodiments, the fluidic substrate and/or the lid comprises at least one through-hole for application of a biochemical reagent to at least one region of the micro-fluidic component or to at least one region of the lid.

According to some embodiments, the lid is attached, for example bonded or clamped, to the fluidic substrate using a lithographically patterned polymer.

According to some embodiments, when the lid is bonded to the fluidic substrate using a bonding layer, the bonding layer enables bonding at low temperatures and voltages. These conditions do not damage the lid, neither do they damage reagents or for example proteins which may be provided on or in the fluidic substrate.

According to some embodiments, the device may further comprise metal contacts electrically connected to the lid for read-out of electrical signals generated by the fluid and captured by measurement systems in the lid. According to some embodiments, the lid of the device may further comprise active pixels, e.g. CMOS pixels, for readout of optical signals from the fluid.

According to some embodiments, at least part of the fluidic substrate and/or the lid is fabricated from a transparent material to allow optical inspection of a fluid sample in the micro-fluidic component.

According to some embodiments, the shape of the device allows insertion into a mobile communication device.

The embodiments described herein allow for the shape or dimensions of the device to be chosen according to standards, e.g. according to standards of memory cards used in mobile devices such as for example: CompactFlash, SmartMedia, MultiMedia Card, Secure Digital memory cards or any other type.

In a second aspect, embodiments of the present disclosure relate to a method for fabricating a device for analyzing a fluid sample. The method comprises: providing a fluidic substrate; providing a lid; attaching the fluidic substrate to the lid to close the fluidic substrate at least partly. The fluidic substrate is a glass fluidic substrate and the lid is microchip. The fluidic substrate may be attached to the lid using a semiconductor bonding process, e.g. a CMOS compatible bonding process.

According to some embodiments, providing a fluidic substrate may comprise: providing a glass substrate, providing a mask layer on the glass substrate, patterning the mask layer so as to create fine structures in the mask layer; providing a first protection layer to protect the patterned mask layer; patterning coarse structures; etching of the coarse structures; growing a second protection layer for protecting coarse structures in a second patternable mask layer; etching the coarse structures in the glass substrate through the second patterned mask layer; growing a second protection layer for protecting the etched coarse structures; removing the first protection layer and etching the fine structures using the second protection layer as an etch mask; and removing the second protection layer.

The embodiments described herein allow for the dimensions of the fine and coarse structures to be precisely controlled. For example e.g. correctly dimensioning the microfluidic channels and/or micro-pillar sizes and distances which are present in the micro-fluidic component.

Moreover, some embodiments enable fine structures with a high aspect ratio. As a result, these embodiments provide a precise control over the flow of a fluid sample in the micro-fluid component may be achieved. In addition, this allows implementation of more complex biochemical reactions than the simple flow used in existing lateral flow immunoassay tests. The combination with the functions implemented in the microchip bonded or clamped as a lid onto the fluidic substrate further adds temperature control, electrical fluid actuation and valving, integrated biosensing and read out where needed. Therefore it becomes possible to implement complex assays, including DNA/RNA assays, proteins, small molecules and cells and combinations thereof in one integrated capillary system starting from body fluids. Moreover, controlled lateral flow and control over the temperature and flow rate results in more accurate point of care test results.

According to some embodiments, providing a fluidic substrate may comprise providing a glass substrate, providing a plurality of masks on top of one another and using each mask for creating microfluidic structures of different depths.

In accordance with particular embodiments of the present disclosure, providing a fluidic substrate may comprise providing a glass substrate, providing a first mask, patterning microfluidic structures, etching the substrate to single depth, providing a second mask, patterning microfluidic structures, etching the substrate to a second depth, and, if required, repeating these steps for creating multiple depths of microfluidic structures.

According to particular embodiments, the fluidic substrate and the lid of a device according to embodiments of the present disclosure may be part of a larger fluidic package, which may be made from different materials like for instance polymers, and which may contain larger fluidic structures, reagents, fluidic and electrical interfaces. This allows the system to become more cost efficient.

According to some embodiments, surfaces of the fluidic substrate and the lid may be partially or fully coated to modify surface interactions of the substrate with the fluid sample.

In a third aspect, the present disclosure provides the use of a device as described in the first aspect of the present disclosure and its embodiments, to perform microscopy. Microscopy may be implemented by using the lid for detecting lens-free images according to the principles of digital holography.

According to a fourth aspect of the disclosure, a packaged device is presented. The package encapsulates the device described in embodiments of the first aspect of the disclosure. According to an example embodiment, the package further comprises a sealed fluidic compartment adapted to be fluidically connected to the micro-fluidic component when opened. According to an example embodiment, the package further comprises electronic circuitry electrically connected to the micro-chip of the device.

The use of the device as described may perform multiomic analysis in which the fluidic substrate is used for performing multiple assays in multiple channels and chambers, and the lid comprising the microchip is used to detect multiple signals from all assays. Those signals can combine multiple DNA, RNA, small molecule, cell signals from a same analyte.

In particular embodiments, the device is used as a single use disposable device for analysis of a small amount of fluid.

In a fifth aspect, the data from the lid may be sent to a smart device such as for instance a smart handheld device, e.g. a smartphone, for instance using a wireless connection. The smart device can be used for processing, visualizing and/or transferring the data.

In some embodiments, the combined data gathered from a single same sample may be used in a software algorithm for calculating a parameter correlating to disease or well-being of an individual.

Some aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

BRIEF DESCRIPTION OF THE FIGURES

The above, as well as additional, features will be better understood through the following illustrative and non-limiting detailed description of example embodiments, with reference to the appended drawings.

FIG. 11-FIG. 17 schematically illustrate method steps of a method to fabricate a fluidic substrate for use in a device, according to an example embodiment.

FIG. 29 schematically illustrates a top view of a part of a micro-fluidic component for use in a device, the micro-fluidic component comprising micro-pillars, according to an example embodiment.

FIG. 30 schematically illustrates a 3D view of a part of the micro-fluidic component of FIG. 29, according to an example embodiment.

Figure 1:
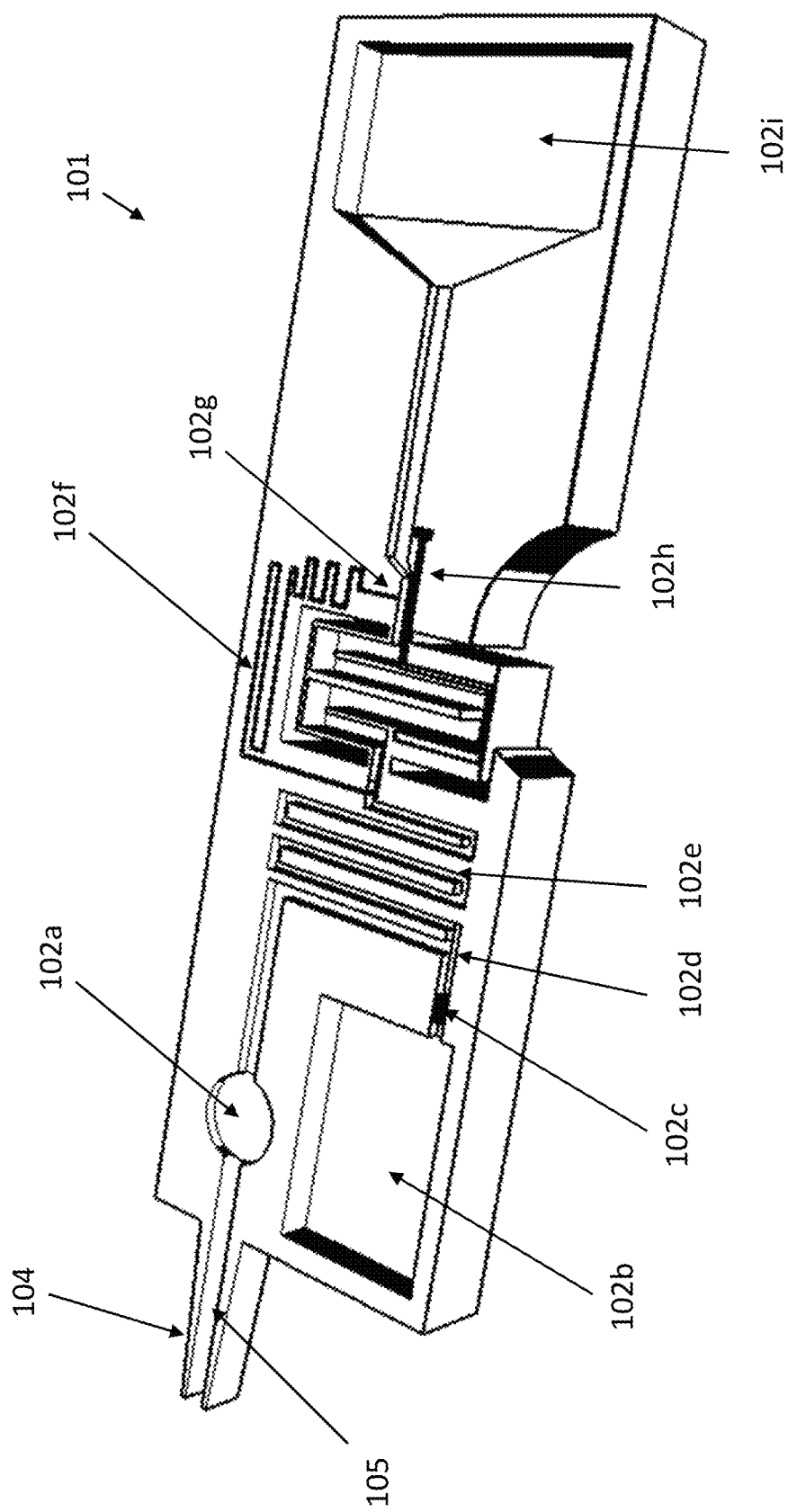
FIG. 1 illustrates a schematic 3D view of a fluidic substrate, according to an example embodiment.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments, various features are sometimes grouped together in a single embodiment, figure, or description thereof for the purpose of streamlining the disclosure and aiding in the understanding of one or more of the various aspects. This method of disclosure, however, is not to be interpreted as reflecting an intention that the claimed embodiments require more features than are expressly recited in each claim. Rather, as the following claims reflect, aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that some embodiments may be practiced without these specific details. In other instances, well-known methods, structures and techniques have not been shown in detail in order not to obscure an understanding of this description.

In some embodiments, where reference is made to a "fluid sample", reference is made to any human or animal body fluid such as blood, urine, saliva.

In some embodiments, where reference is made to an "I/O pad" or an "I/O contact", reference is made to a contact such as a metal contact allowing input and output of electrical signals of a micro-chip.

In some embodiments, where reference is made to "CMOS", reference is made to a Complementary Metal-Oxide Semiconductor.

In some embodiments, where reference is made to "glass" reference is made to a non-crystalline amorphous solid at the atomic scale that exhibits a glass transition when heated towards the liquid state. In some embodiments, "glass" may refer to silicate glasses, like for example quartz, boro-silicate glass, etc. An advantage of silicate glasses is their optical transparency. Glass in addition can transmit, reflect and refract light; moreover these qualities may be enhanced by cutting and polishing. Glass substrates used in some embodiments may be colored, for instance by adding metallic salts, and may also be painted. Although brittle, silicate glass is extremely durable, can be formed or molded into any shape, and is a sterile product. As a result, several material properties of glass and reproducible electro-osmotic flow properties make it a very attractive material for use in microfluidic systems.

In some embodiments, where reference is made to "micro-fluidic" reference is made to fluidic devices having device sizes typically below 1 mm.

In some embodiments, where reference is made to "lab-on-a-chip device", reference is made to devices that integrate one or more laboratory function on a single chip.

Throughout the description reference may be made to "particles". This may refer to particles of biological nature, for example cells or biomolecules. In a first aspect the present disclosure relates to a device 100 for analyzing a fluid sample, as for instance illustrated in FIG. 26. The device 100 may be defined as a medical device. In some embodiments, the device 100 comprises: a fluidic substrate 101 and a lid 103 attached to the fluidic substrate 101 at least partly covering the substrate 101.

The fluidic substrate 101 comprises a micro-fluidic component 102. In some embodiments, a micro-fluidic component 102 may comprise, as schematically illustrated in a detailed 3D drawing in FIG. 1, a plurality of microfluidic components such as an inlet, the inlet comprising a sample pad 102a, a reagent storage 102b, a hermetic valve 102c, whereby the hermetic valve is suited for one-time usage, a first trigger valve 102d, a mixer 102e, a delay line 102f, a second trigger valve 102g, an heater 102h and a wick 102i. The microfluidic component is embedded in the fluidic substrate 101 and configured to propagate a fluid sample through the micro-fluidic component 102; and a means 109 for providing a fluid sample connected to the micro-fluidic component 102. The lid 103, by at least partly covering the substrate 101, at least partly closes the micro-fluidic component 102. In some embodiments, the fluidic substrate 101 is a glass fluidic substrate; and the lid 103 is a microchip, e.g. a CMOS chip.

In embodiments where the fluidic substrate 101 is a glass substrate and the lid 103 is a microchip, both can be manufactured using mass production process technologies, like for example CMOS compatible processing techniques. Cheap packaging techniques may be used to attach, e.g. bond, the glass substrate to the lid, e.g. microchip. This may reduce the total cost of the device and allow it to be used as a disposable device and produced in high volume.

Figure 26:
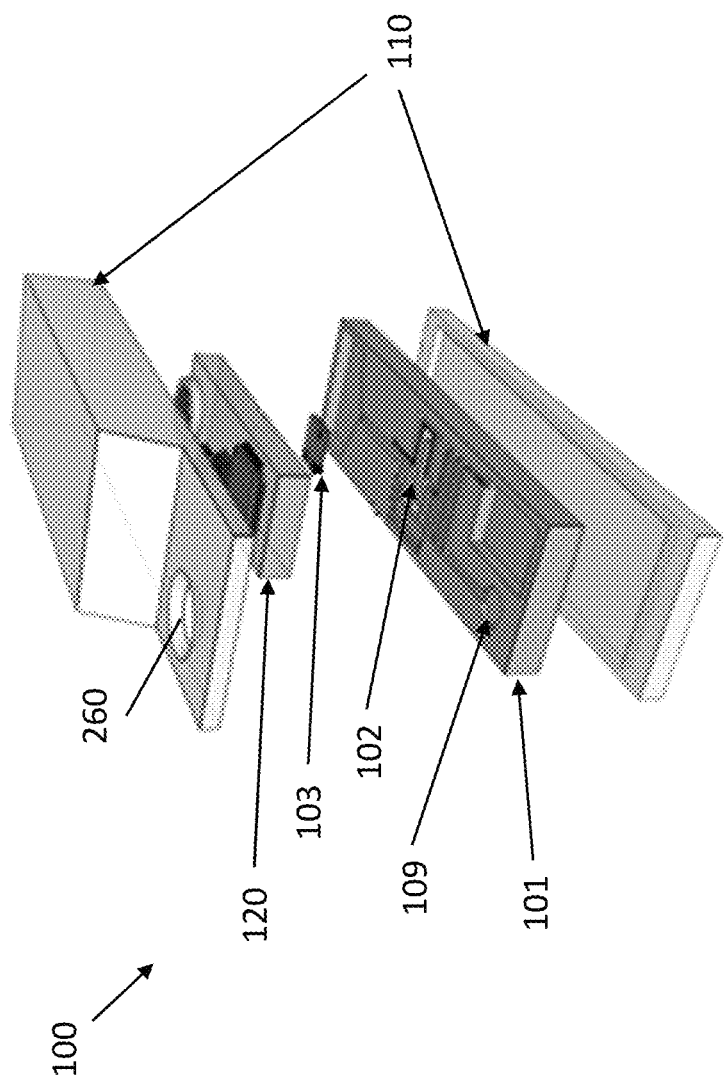
FIG. 26 schematically illustrates a 3D view of a wireless stand-alone device, according to an example embodiment.

According to an example embodiment, the lid, e.g. microchip, 103 at least partly closes or covers the fluidic substrate 101. Other parts of the fluidic substrate 101 may be closed or covered by other means. For example, the other parts of the fluidic substrate 101 may be closed by a printed circuit board (PCB) 120 which is electrically connected to the lid, e.g. microchip 103 (which is illustrated in FIG. 26 and described further below). Further, other parts of the fluidic substrate 101 may be closed by a package which encapsulates the device 100. Due to capillary forces present in the micro-fluidic component 102, some parts of the micro-fluidic component 102 may remain open. For example, like in embodiments where the entire or complete micro-fluidic component 102 is open except for the lid, e.g. microchip, 103 covering a part such that it may be in direct contact with a fluid sample in the micro-fluidic component 102.

Figure 3:
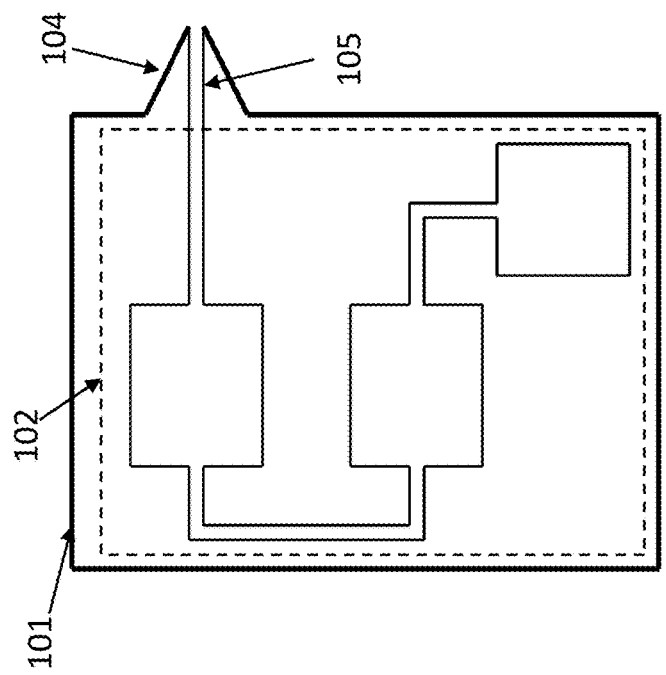
FIG. 3 schematically illustrates a top view of a fluidic substrate without a lid used in the device of FIG. 2.
Figure 2:
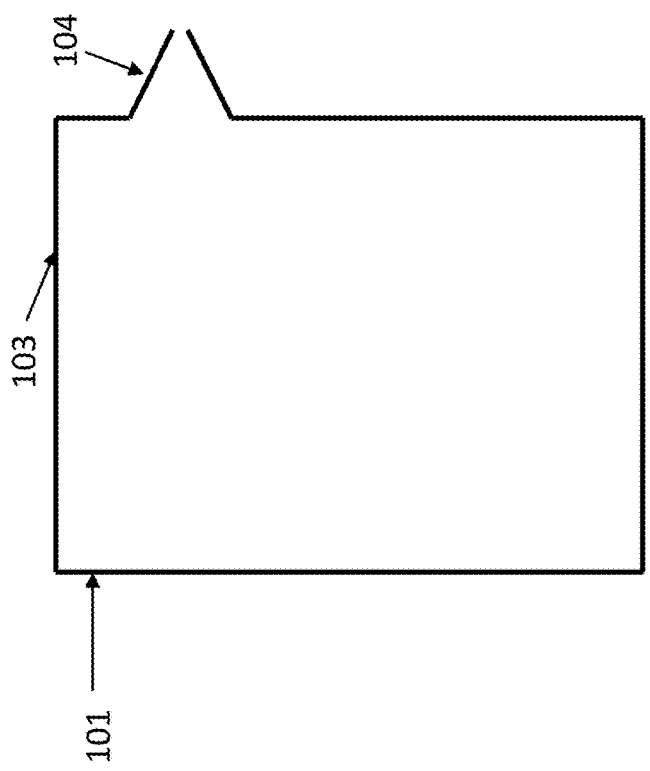
FIG. 2 schematically illustrates a top view of a device for analyzing a fluid sample, according to an example embodiment.
Figure 4:
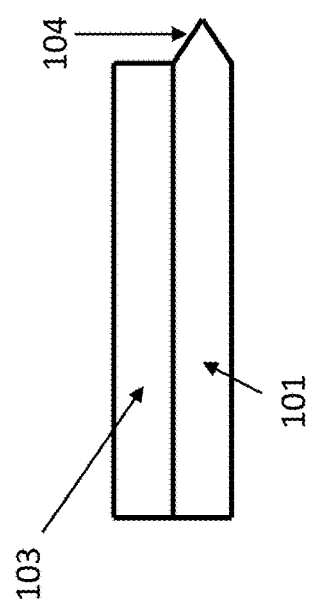
FIG. 4 schematically illustrates a side view of the device of FIG. 2.

A top view of an embodiment of a device 100 is schematically illustrated in FIG. 2, whereby the fluidic substrate 101 and the lid 103 are attached to one another. In FIG. 2 the fluidic substrate 101 further may comprise a means for providing a fluid sample 104. A top view of an exemplary fluidic substrate 101 used in the device of FIG. 2 is schematically illustrated in FIG. 3. A side view of an embodiment of the device 100 of FIG. 2 where the fluidic substrate 101 is attached to the lid 103 is schematically illustrated in FIG. 4.

Figure 27:
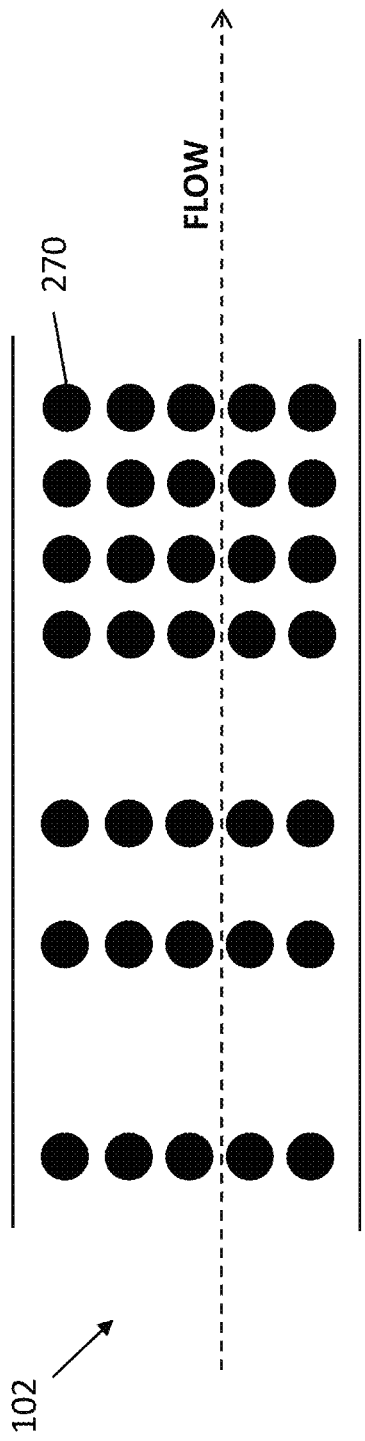
FIG. 27 schematically illustrates a top view of a part of a first embodiment of a micro-fluidic component, the micro-fluidic component comprising micro-pillars, according to an example embodiment.
Figure 28:
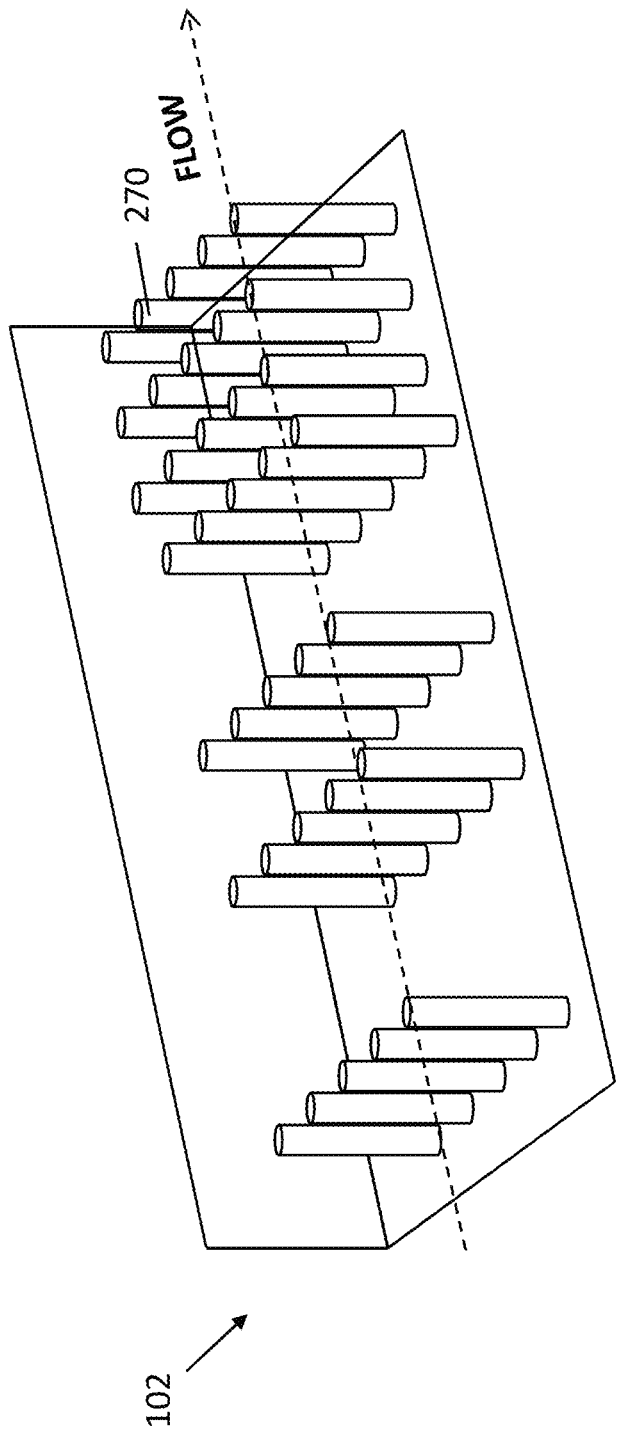
FIG. 28 schematically illustrates a 3D view of a part of the micro-fluidic component of FIG. 27, according to an example embodiment.

A device 100 comprises a fluidic substrate 101 which is attached, for example bonded or clamped, to a lid 103, whereby the lid 103 at least partially covers the fluidic substrate 101. The fluidic substrate 101 comprises a micro-fluidic component 102. The micro-fluidic component 102 may comprise micro-fluidic channels, micro-reactors or other micro-fluidic parts/structures which are interconnected to allow a fluid sample to propagate through the complete micro-fluidic component 102. The micro-fluidic component 102 may comprise a plurality of micro-pillars or microstructures at regular or irregular distances to allow at least one of the following functionalities: filtering and separation, valve functionality or "valving", mixing of a fluid sample during propagation through the micro-fluidic component. FIG. 27 schematically illustrates a top view of a part of an open micro-fluidic component 102 comprising a pillar array, the pillar array comprising micro-pillars 270 to allow filtering and separation, valving, mixing of a fluid sample during propagation through the micro-fluidic component. FIG. 28 schematically illustrates a 3D view of the open micro-fluidic component 102 embodiment of FIG. 27 comprising micro-pillars 270. The micro-pillars 270 in FIG. 27 and FIG. 28 are positioned in such a way as to enable or form a gradient for the to-be-examined fluid sample. This gradient allows the filtering out of larger particles in a first part of the micro-fluidic component 102 and the filtering out of smaller particles in a second part of the micro-fluidic component 102. FIG. 29 and FIG. 30 schematically illustrate another embodiment of a gradient of micro-pillars 270 in the micro-fluidic component 102. FIGS. 27-30 illustrate micro-pillars having a cylindrical shape; however, the present disclosure is not limited thereto.

According to some embodiments, the micro-fluidic component 102 may be configured to create a capillary action to propagate a fluid sample through the device 100. The dimensions of the micro-fluidic component 102 may be adapted to create a capillary action in the micro-fluidic component 102 when a fluid sample is present. For example, dimensions and distance between micro-pillars 270 in the micro-fluidic component 102 may be configured to create a capillary action in the micro-fluidic component 102. The device 100 might not need additional active components (e.g. an active separate pump) to propagate a fluid sample through the device 100. Thus, the complexity of the device 100 is reduced compared to conventional implementations, which further reduces fabrication cost and power consumption. As the costs to fabricate are low, the device may be used as a disposable fluid analysis device.

According to some embodiments, the fluidic substrate 101 may comprise a vacuum element or compartment which is connectable to the micro-fluidic component 102. When a fluid sample is provided to the micro-fluidic component 102, an air-tight connection between the vacuum compartment and the micro-fluidic component can be realized. By connecting the vacuum compartment to the micro-fluidic component, hence by opening the vacuum compartment, a suction force is generated in the micro-fluidic component 102 thereby realizing propagation of a fluid sample through the micro-fluidic component 102.

The air-tight connection between the vacuum compartment and the micro-fluidic component may be realized by for example opening an air-tight valve which is present between the vacuum compartment and the micro-fluidic component. The air-tight valve seals the vacuum compartment as long as it is closed.

Alternatively, the air-tight connection between the vacuum compartment and the micro-fluidic component may be realized by removing an element which is present between the vacuum compartment and the micro-fluidic component. The element seals the vacuum compartment from the micro-fluidic component as long as it is present. The element may be removed by supplying a voltage or a current pulse to the element. The element may be a membrane comprising a resistor configured to destruct the membrane when a voltage or current pulse is supplied to the resistor. The resistor may be positioned in or on the membrane. The resistor may also be positioned on the fluidic substrate 101 such that the membrane may be destroyed when the resistor is powered. Trenches in the fluidic substrate 101 may be present around the resistor for reducing heat dissipation in the fluidic substrate 101. The element may also comprise a meltable material which may be melted at a suitable temperature depending on the material used, by a heating element positioned near the element, e.g. on the fluidic substrate. By melting the material, the compartment is opened towards the micro-fluidic component.

Some embodiments allow for precise control over the flow of a fluid sample in the micro-fluidic component 102 to be achieved by e.g. correctly dimensioning the micro-fluidic channels and/or micro-pillar sizes and distances which are present in the micro-fluidic component 102. Lithographic patterning may be used to fabricate the micro-fluidic component 102 in the fluidic substrate 101. The lithographic patterning of micro-pillars and micro-fluidic channels of the micro-fluidic component 102 allows for accurate control of the dimensions, size and shape of the micro-pillars and micro-fluidic channels, thereby precisely controlling the capillary flow. This precise control over the dimensions, achievable via lithographic processes presents an advantage in achieving more reproducible lateral flow than conventional lateral flow test strips, which are made from porous paper with uncontrolled lateral flow. By varying the dimensions over the length of the device it is possible to slow down and/or to increase the speed of the flow of a fluid sample where desired. This allows implementation of more complex biochemical reactions than the simple flow used in existing lateral flow immunoassay tests. The combination with the functions implemented in lid 103, e.g. a microchip, bonded or clamped onto the fluidic substrate 101 further adds temperature control, electrical fluid actuation and valving, integrated biosensing and read out where needed. Therefore it becomes possible to implement complex assays, including DNA/RNA assays, proteins, small molecules and cells and combinations thereof in one integrated capillary system starting from body fluids. Moreover, controlled lateral flow and control over the temperature and flow rate results in more accurate point of care test results.

In some embodiments, the fluidic substrate 101 comprises a means 104, 109 for providing a fluid sample which is connected to the micro-fluidic component 102.

Figure 25:
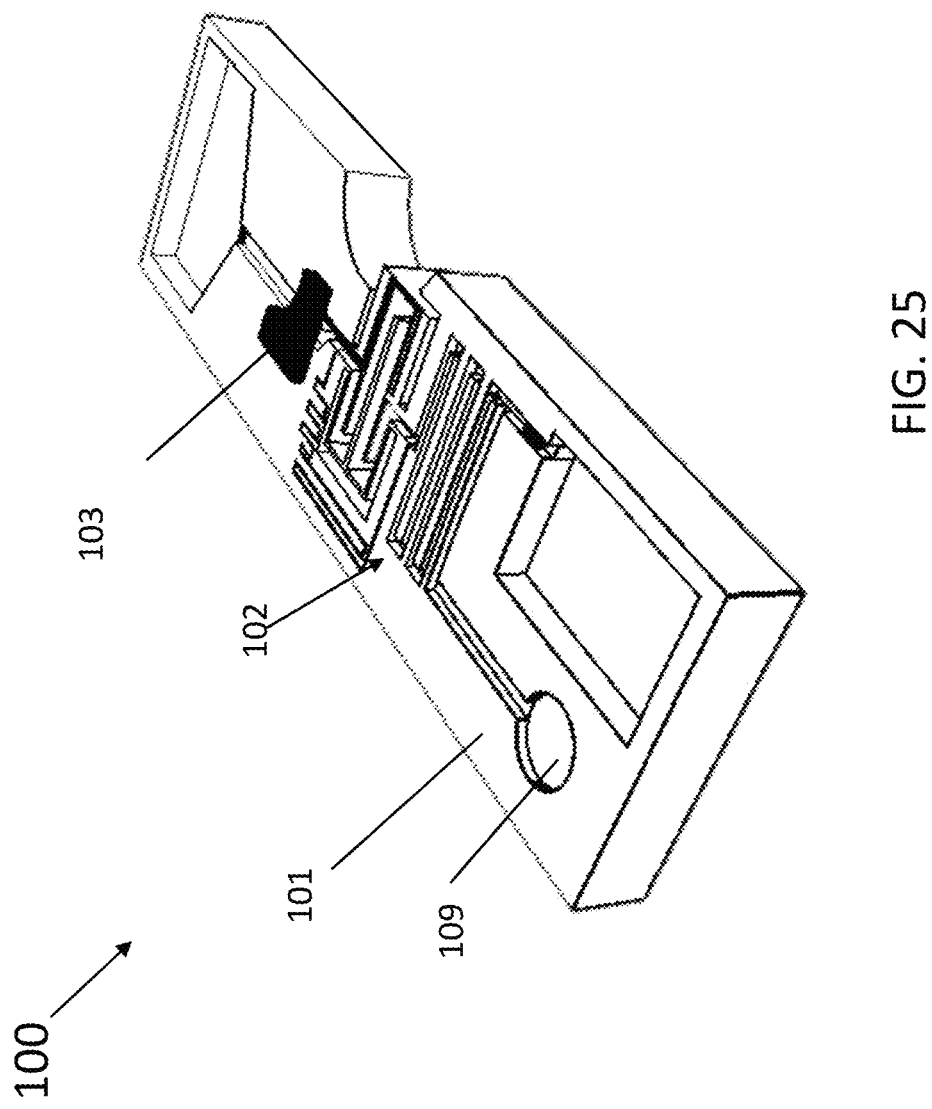
FIG. 25 schematically illustrates a 3D view of a device, according to an example embodiment.

The lid 103 may function as a cover for the fluidic substrate 101 wherein the lid 103 fully or partly closes the micro-fluidic component 102. FIG. 25 schematically illustrates an embodiment wherein the lid 103 partly covers the fluidic substrate 101. In some embodiments, the lid 103 and fluidic substrate 101 are two separate elements attached to each other. The micro-fluidic component 102 may be an open micro-fluidic component 102 in the fluidic substrate 101. According to alternative embodiments, the dimensions of the lid 103 may be identical to the dimensions of the fluidic substrate 101. The lid 103 may fully or also partially be covering the fluidic substrate 101. When the means for providing a fluid sample is an inlet 109 (as illustrated in FIG. 26), for instance a sample pad 102a, the lid 103 may partially cover the fluidic substrate 101, allowing a user to access the means for providing a fluidic sample, for example an inlet 109 to deposit a fluid sample.

According to some embodiments, the device 100 may further comprise one or more electrodes which are placed on the micro-fluidic component 102 of the fluidic substrate 101. These electrodes may be biocompatible and/or transparent electrodes. The electrodes may be electrically connected to the lid 103 and are allowed to interact with a fluid sample in the micro-fluidic component 102 of the device 100 as they may be in direct contact with a fluid sample in the micro-fluidic component 102. While the lid 103 itself may comprise electrodes, it advantageous to separate the electrodes from the lid 103, which may allow the lid 103 to be smaller which reduces costs.

According to some embodiments, the micro-fluidic component 102 may comprise a capillary pump.

According to some embodiments, the means for providing a fluid sample may be an integrated needle 104, for instance fabricated from glass, and comprising an inner fluidic channel 105 connected to the micro-fluidic component 102. The needle 104 may be a protruding portion of the fluidic substrate 101 and may be positioned so as to penetrate skin tissue when pressed against that skin tissue.

The fluidic substrate 101 and the needle 104 may be fabricated from a single piece of glass. This simplifies the fabrication of the device 100, as separate steps to attach a needle 104 to the fluidic substrate 101 are not required and the means for providing a fluid sample 104 is a part of the glass fluidic substrate 101 and thus is also a glass needle 104. Also, standard micro-machining processing techniques may be used to fabricate the needle 104. The needle 104 may be a sharp needle which allows skin tissue to be penetrated. The fluidic substrate 101 and the needle 104 may be both fabricated from glass. The strength of the glass allows the needle 104 to be very sharp which eases the penetration of the needle 104 in skin tissue. Further, the strength of the glass allows skin tissue to be firmly pressed against the needle 104, allowing penetration of skin tissue without bending or breaking of the needle 104.

According to some embodiments, the needle 104 may be positioned in a horizontal plane of the fluidic substrate 101 wherein the needle 104 is positioned on a sidewall of the fluidic substrate 101. The needle 104 may be a protruding portion of a sidewall of the fluidic substrate 101. According to a different embodiment, the needle 104 may be positioned on a horizontal plane of the fluidic substrate 101 wherein the needle is positioned perpendicular on a major surface of the fluidic substrate 101. According to some embodiments, the needle 104 may feature an open channel connected to the micro-fluidic component 102, wherein, in use, the skin tissue functions as a side-wall of the needle 104 when skin tissue is penetrated.

The device 100 may be used by pressing skin tissue of a user against the needle 104. When sufficient force is used, the needle 104 punctures and penetrates the skin tissue, allowing blood to enter the inner fluidic channel 105 of the needle 104. Thus, the blood is not exposed to the environment, resulting in an fluid sample which is minimally contaminated. The needle 104 comprises a tip which is open to allow a fluid sample to enter the inner fluidic channel 105 as illustrated in FIG. 3. When the needle is sharp with a small outer diameter (smaller than 200 μm) the penetration of the skin tissue will not cause any discomfort to the user. As the inner fluidic channel 105 of the needle 104 is connected to the micro-fluidic component 102 of the fluidic substrate 101, blood may enter the micro-fluidic component 102. Due to a capillary force or a suction force being generated by opening a vacuum compartment or seal of the fluidic substrate, the fluid sample, e.g. blood, will propagate through the micro-fluidic component 102.

FIG. 1 illustrates an embodiment of the fluidic substrate 101 with an integrated needle 104 (as part of the fluidic substrate 101), the needle having an inner fluidic channel 105 connected to a micro-fluidic component 102. The micro-fluidic component 102 may comprise: an inlet, e.g. a sample pad 102a, a reagent storage 102b, a possibly one-time usage hermetic valve 102c, a first trigger valve 102d, a mixer 102e, a delay line 102f, a second trigger valve 102g, a heater 102h and a wick 102i. As illustrated in FIG. 1, all fluidic components in the fluidic substrate 101 are open, e.g. are not covered. The lid 103 may function as a cover to close some or all fluidic components 102a-102i of the fluidic substrate 101.

Figure 5:
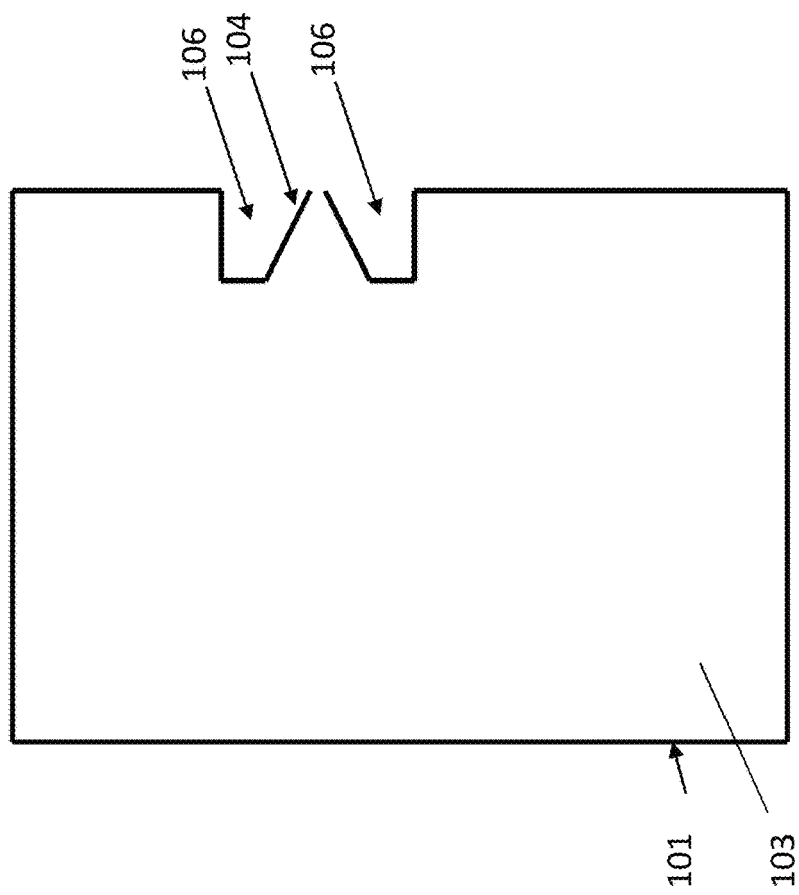
FIG. 5 schematically illustrates a top view of a device for analyzing a fluid sample, featuring a cut-out for a needle, according to an example embodiment.

According to some embodiments, the fluidic substrate 101 may comprise a cut-out 106 as illustrated schematically in FIG. 5, wherein the means for providing a fluid sample, e.g. needle, 104 is positioned in the cut-out 106. The cut-out 106 is a removed part of the fluidic substrate 101 and offers mechanical protection for the needle 104 (against for instance breaking before use) which resides in the cut-out 106 and is protected by it.

Figure 6:
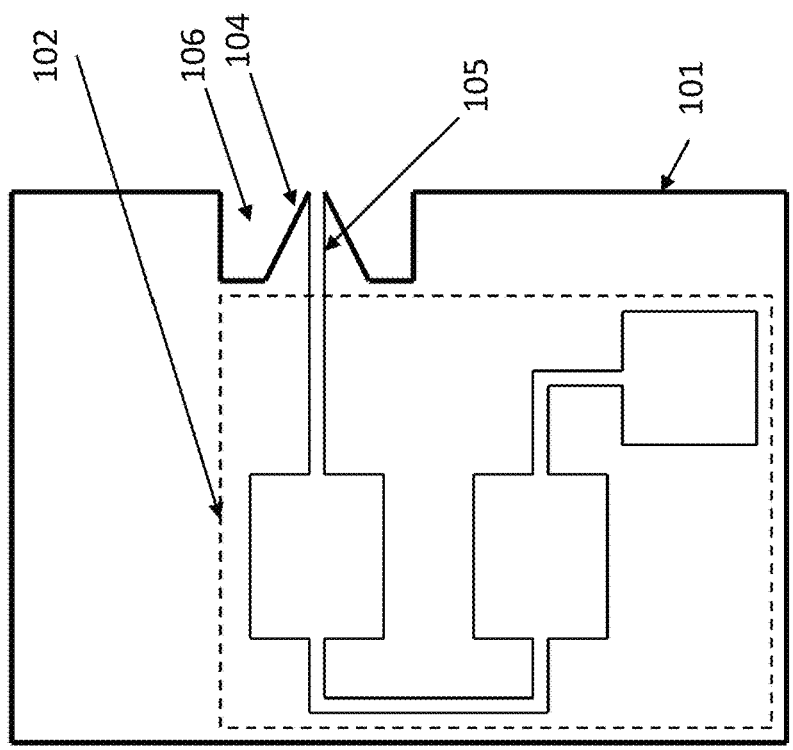
FIG. 6 schematically illustrates a top view of a fluidic substrate featuring a cut-out for a needle without a lid, for use in the device of FIG. 5, according to an example embodiment.

FIG. 5, illustrating a top view of an embodiment, further illustrates that the lid 103 is attached, e.g. bonded or clamped, to the fluidic substrate 101. FIG. 6 schematically illustrates a top view of an exemplary fluidic substrate 101 and micro-fluidic component 102 embedded in the fluidic substrate 101, wherein the fluidic substrate comprises a cut-out 106. In FIG. 6 the means 104 for providing a fluidic sample, e.g. needle, comprises an inner fluidic channel 105, the fluidic channel 105 connected to the micro-fluidic component 102.

Figure 7:
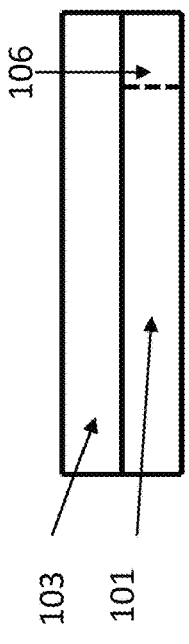
FIG. 7 schematically illustrates a side view of the device of FIG. 5, according to an example embodiment.

FIG. 7 schematically illustrates a side view of an embodiment wherein the lid 103 is attached, e.g. bonded or clamped, to the fluidic substrate 101, the fluidic substrate 101 comprising a cut-out 106. The means for providing a fluidic sample 104 is not shown.

As illustrated in FIGS. 5, 6 and 7, a means for providing a fluid sample, e.g. a needle 104, is located in a cut-out 106 of the fluidic substrate 101. The cut-out 106 protects the needle 104 from breaking e.g. when the device 100 is inserted in a slot of an external device, e.g. a mobile device such as a smartphone, for instance for readout. The sidewall of the fluidic substrate 101 may feature the cut-out 106. The needle 104 may be positioned in the cut-out 106 to allow a user to penetrate skin tissue when pressed firmly against the cut-out 106. When in use, the skin will fill the cavity of the cut-out, and the needle 104 can puncture and penetrate the skin. During fabrication, the needle 104 may be fabricated while fabricating the cut-out 106, e.g. when material is removed from the fluidic substrate to generate a cut-out, this is done such that a needle shape within a cavity or cut-out region remains after removal of the material. As a result, less material is wasted as only the material for the cut-out 106, excluding the material for the needle 104, needs to be removed. The cut-out 106 and needle 104 may be fabricated using standard micromachining processing techniques.

Figure 9:
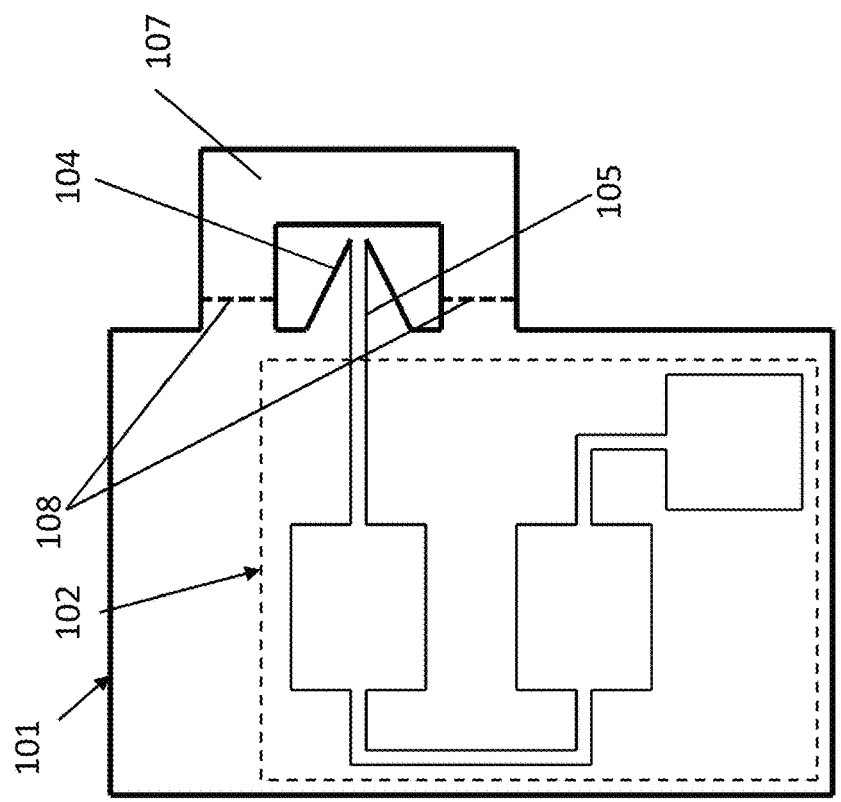
FIG. 9 schematically illustrates a top view of a fluidic substrate featuring a protection structure for a needle, for use in the device of FIG. 8 without a lid, according to an example embodiment.
Figure 8:
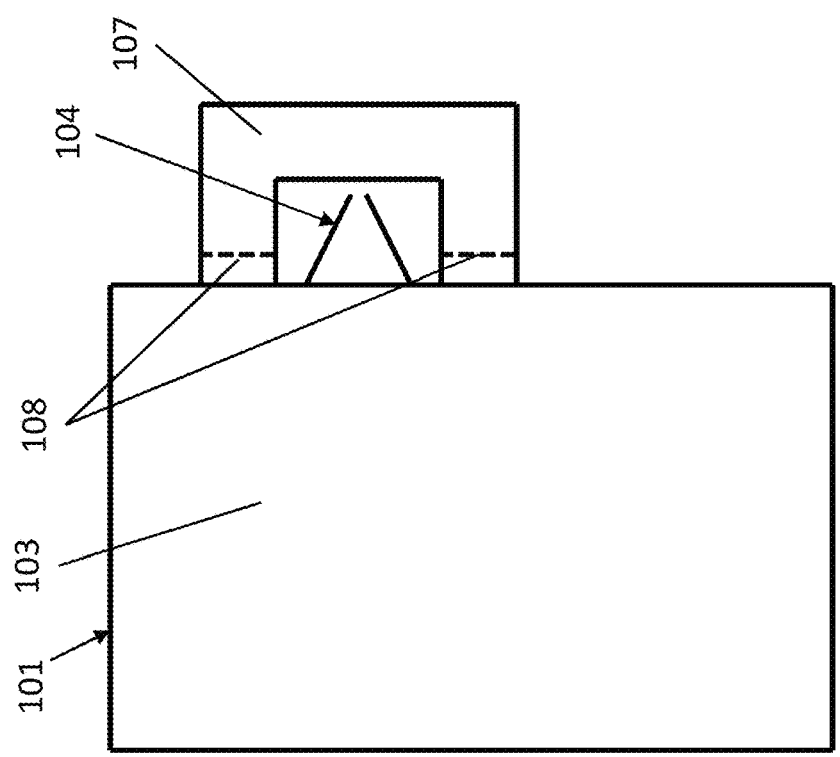
FIG. 8 schematically illustrates a top view of a device for analyzing a fluid sample, featuring a protection structure for a needle, according to an example embodiment.
Figure 10:
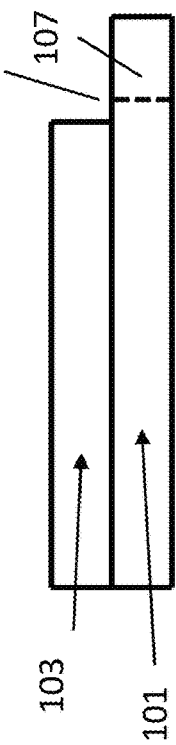
FIG. 10 schematically illustrates a side view of the device of FIG. 8, according to an example embodiment.

According to some embodiments, the fluidic substrate 101 may comprise a protection structure 107 (in addition to or as an alternative to the cut-out 106) for protecting the needle 104, removably attached to the fluidic substrate 101. According to some embodiments, the protection structure 107 may be attached to the fluidic substrate 101 via at least one anchoring mechanism 108. The protection structure 107 may be detached by breaking the at least one anchoring mechanism 108. The protection structure 107 may be part of the fluidic substrate 101 wherein the anchoring mechanism 108 is a groove in the fluidic substrate 101 to allow breaking of the protection structure 107 at the groove and exposing the needle 104. FIG. 8 is a schematic top view of such an embodiment of a device 100, the device comprising a fluidic substrate 101, a needle 104, the needle comprising an inner channel 105, and a protection structure 107, protecting the needle 104, whereby the protection structure is attached to the fluidic substrate 101 via the at least one anchoring mechanism 103. In FIG. 8 the fluidic substrate 101 is covered by a lid 103. As can be seen in FIG. 9 (illustrated is a schematic top view of an exemplary embodiment of a fluidic substrate 101 for use in a device according to embodiments of the present disclosure, for instance a device as illustrated in FIG. 8), the protection structure 107 is part of the fluidic substrate 101 and features two anchoring mechanisms 108 which allow detaching of the protection structure 107 from the fluidic substrate 101. FIG. 9 further illustrates a micro-fluidic component 102 connected to the needle 104, whereby the micro-fluidic component is uncovered or open (e.g. where no lid 103 is attached to the fluidic substrate. FIG. 10 schematically illustrates a side view of the device 100 of FIG. 8.

According to alternative embodiments, the means for providing a fluid sample is an inlet 109. The inlet 109 may be an indentation, for example circular, in the fluidic substrate 101 which is connected to the micro-fluidic component 102 by a fluidic channel. To use the device, a user may deposit a drop of a fluid sample, e.g. a bodily fluid such as blood or saliva, on the inlet 109 of the device, for example via a through-hole 260 provided in the package of the device as illustrated in FIG. 26. Due to capillary force or a suction force generated by opening a vacuum compartment of the fluidic substrate or by removing an element which is present between the vacuum compartment and the micro-fluidic component, the fluid sample, e.g. a bodily fluid, will propagate through the micro-fluidic component 102, without the use of an additional capillary pump.

FIG. 26 schematically illustrates a de-assembled device 100, comprising a fluidic substrate 101 comprising an inlet 109 and a microfluidic component 102, a lid 103 and a package 110. The package 110 may comprise a base part and a top part which can be assembled together to package the device 100, the device comprising the fluidic substrate 101 and the lid 103 at least partially covering the fluidic substrate, thus protecting these from environmental influences such as dust or other contaminants. The package may comprise clamps for clamping the device 100 inside the package. The package may comprise a through-hole 260 for depositing a fluid sample on means for providing the fluid sample, e.g. an inlet 109 of the fluidic substrate 101. When all parts are assembled, the device 100 may function as a stand-alone wireless device for analyzing a fluid sample. The package may further comprise a PCB 120 electrically connected to the lid, e.g. microchip 103. The PCB may comprise electronic circuitry for wirelessly transmitting data originating from the lid, e.g. microchip 103. The PCB may further comprise one or more processors for processing data originating from the lid, e.g. microchip. By processing the data on-board, the size of the transmitted data can be reduced resulting in lower power usage.

According to some embodiments, at least a part of the lid 103 may be in contact with the fluid sample when the fluid sample is present in the device 100 or when the device 100 is in use.

In some embodiments, the lid 103 is a microchip, electronic circuitry present on a surface of the chip may be in direct contact with the fluid sample when the lid 103 is functioning as a side-wall of an open micro-fluidic component 102 in the fluidic substrate 101. In this case, the side of the lid 103, e.g. microchip comprising electronic circuitry may be bonded or clamped to an open micro-fluidic component 102 of the fluidic substrate 101 wherein the electronic circuitry is aligned with parts of the micro-fluidic component 102 where interaction with a fluid sample is desired. This may improve the interaction between the electronic circuitry and the fluid sample. According to some embodiments, the lid 103 may comprise bonding layers to enable bonding of the lid 103 to the fluidic substrate 101. According to some embodiments, a first side of the fluidic substrate 101 comprising an open micro-fluidic component 102 may be attached, e.g. bonded or clamped to a first side of the lid 103 and over its entire surface, where the lid 103, e.g. microchip, comprises at least one electrical component. According to an embodiment, the lid 103 may comprise a transistor layer, the transistor layer being electrically connected to at least one electrical component, the electrical component being at least one of the following: biosensing circuitry, biosensing circuitry for fluorescent detection, biosensing circuitry for lens-free detection of particles, electrodes for sensing purposes, electrodes for fluid manipulation purposes, circuitry for data communication purposes, circuitry for wireless data communication purposes, temperature sensors, heater electrodes for temperature control or temperature cycling and fluid sensors and electrodes for fluidic viscosity control. The circuitry for wireless data communication may comprise provisions for communication via a Bluetooth radio or a WiFi module for wirelessly transmitting data from electronic circuitry in the lid 103. The device 100 may communicate with an external device such as a mobile device which may be used to further process the data.

According to some embodiments, the lid 103 is a microchip, e.g. a CMOS chip. According to some embodiments, the microchip may comprise a glass substrate 111, a transistor layer 112, at least one electrical component electrically connected to the transistor layer 112 and at least one bonding layer 115. The at least one electrical component may be biosensing circuitry, biosensing circuitry for fluorescent detection, biosensing circuitry for lens-free detection of particles, electrodes for sensing purposes, electrodes for fluid manipulation purposes, circuitry for data communication purposes, circuitry for wireless data communication purposes, temperature sensors, heater electrodes for temperature control and fluid sensors and electrodes for fluidic viscosity control. The at least one electrical component may be aligned with at least a part of the micro-fluidic component thereby increasing accuracy.

Figure 18:
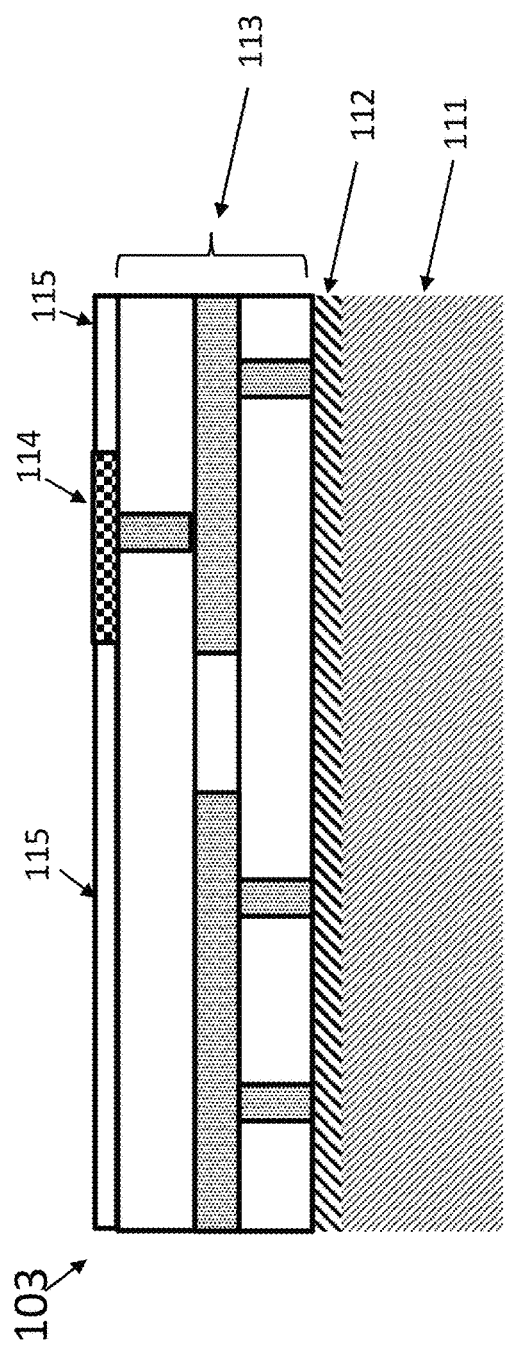
FIG. 18 schematically illustrates a microchip for use in a device, according to an example embodiment.

A particular embodiment of a lid 103 is schematically illustrated as a side view in FIG. 18. In this embodiment, a lid in the form of a microchip 103 is provided, whereby the microchip 103 comprises a glass substrate 111. Atop the glass substrate 111 a transistor layer 112 may be present. Atop the transistor layer 112 an interconnection layer 113 may be present. Atop the transistor layer 112, at least one electrical component may be present, for example a bonding layer 115 and/or at least one electrode 114, electrically connected to the transistor layer 112 via the interconnection layer 113. The interconnection layer 113 may comprise a plurality of layers, which may be metal layers. According to some embodiments, atop the transistor layer 112 and the interconnection layer 113, a bonding layer 115 and at least one electrode 114 may be present. The electrode 114 may be electrically connected to the transistor layer via the interconnection layer 113.

According to some embodiments, the at least one electrical component may be a biocompatible electrode which is fluid corrosion free and chemically inert. According to a specific embodiment, the at least one electrode 114 is TiN electrode.

According to some embodiments, the bonding layer 115 may be a layer which allows attachment, e.g. bonding, of the microchip 103 to the fluidic substrate 101, at low temperatures and voltages. These conditions do not damage the microchip, neither do they damage reagents or for instance proteins which may be provided on the microfluidic substrate 101. According to a specific embodiment, the bonding layer 115 may be a suitable layer like for example SiO2 or polymer layer.

Figure 19:
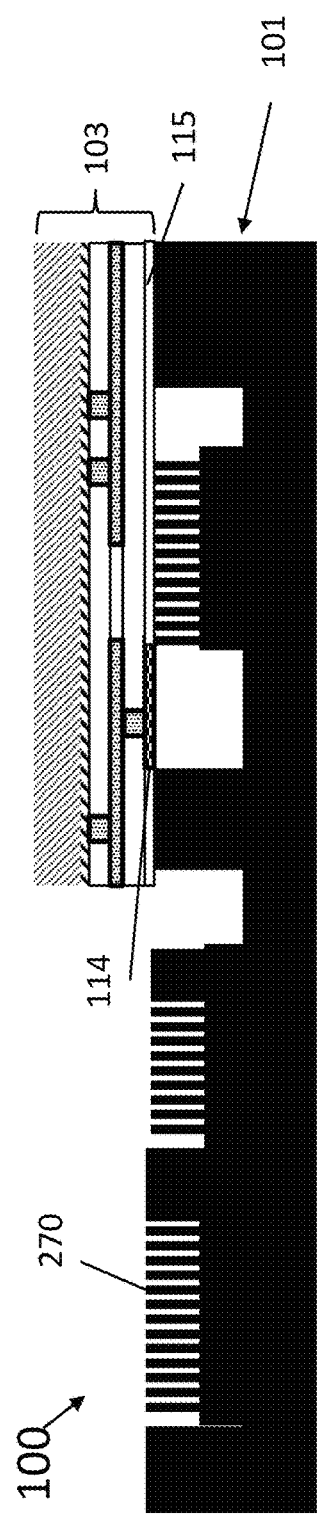
FIG. 19 schematically illustrates the bonding of a microchip with a fluidic substrate, according to an example embodiment.

FIG. 19 schematically illustrates a side view of a device 100, wherein a lid, for example a microchip 103 as illustrated in FIG. 18, is bonded or clamped to a fluidic substrate 101. The fluidic substrate 101 is partly closed by the microchip 103. The side of the microchip 103 comprising the bonding layer 115 and the electrode 114 is bonded or clamped to the side of the fluidic substrate 101 comprising an open micro-fluidic component 102 comprising an array of pillars 270, whereby the microchip 103 covers or closes the micro-fluidic component 102 at least partially. This means that the microchip 103 as illustrated in FIG. 18 is flipped upside down with respect to its position as illustrated in FIG. 18. The electrode 114 is thereby in direct contact with a fluid sample when present in the micro-fluidic component 102. The bonding layer 115 is used to attach the microchip 103 to the micro-fluidic component 103 embedded in the fluidic substrate 101.

Figure 20:
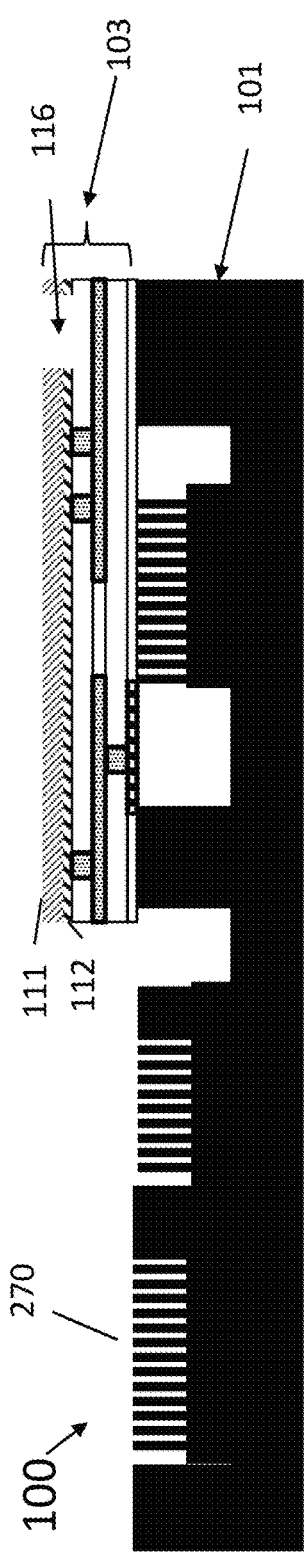
FIG. 20 schematically illustrates the bonding of a microchip with a fluidic substrate, wherein the microchip comprises a silicon I/O interconnect, according to an example embodiment.

According to some embodiments, the lid, e.g. microchip 103, may comprise at least one I/O connection, which may be a silicon I/O connection 116, as illustrated schematically in the lid 103 attached to the fluidic substrate 101 in FIG. 20. The silicon I/O connection 116 may be a backside opening through the substrate 111 of the microchip to access electrical signals of the microchip 103 in the transistor layer 112. Further, in yet alternative embodiments, the I/O connection, which may be silicon I/O connection 116, may be a backside opening through both the substrate 111 and the transistor layer 112 of the microchip to access electrical signals of the microchip 103 in the interconnection layer 113. FIG. 20 also illustrates the device 100 comprising a microchip as lid, wherein the microchip 103 is bonded or clamped to a fluidic substrate 101 and wherein the microchip 103 features a silicon I/O connection 116 through both the substrate 111 and the transistor layer 112.

According to some embodiments, the fluidic substrate may comprise an open micro-fluidic component 102 and the fluidic substrate may be covered partly by a lid, for example a microchip 103. In some embodiments, a part of the micro-fluidic component 102 need not be covered or remain open as this allows reagents to be applied/spotted on specific open parts of the micro-fluidic component 102. In this case, no extra through-holes are needed to apply reagents after bonding of the fluidic substrate 101 to the microchip 103. In some embodiments, the microchip area may be smaller, as the active electronics is the more expensive part of the disposable device.

According to some embodiments, when the lid is a microchip 103, the latter may further comprise at least one I/O pad 117 (like for example illustrated further in FIG. 27). The at least one I/O pad 117 may be located on the interconnection layer 113 such that the I/O pad with at least one electrode can be bonded or clamped to the fluidic substrate. The I/O pad 117 is electrically connected to the transistor layer through the interlayer.

Figure 21:
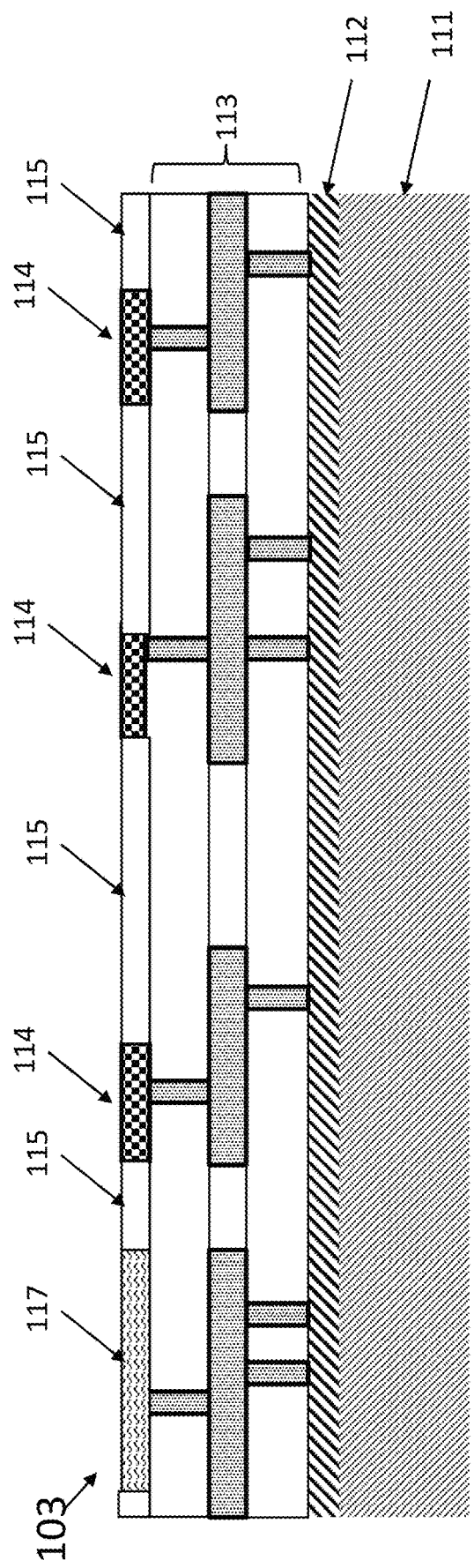
FIG. 21 schematically illustrates a microchip for use in a device, the microchip comprising an I/O pad, according to an example embodiment.

FIG. 21 illustrates an embodiment of a lid 103, wherein the lid is a microchip 103. The microchip 103 may comprise a glass substrate 111. Atop the glass substrate a transistor layer 112 is present. Atop the transistor layer 112, an interconnection layer 113 is present. The interconnection layer 113 may comprise a plurality of layers, which may be metal layers, to interconnect the transistor layer 112 with electrical components. Atop the transistor layer 112, a bonding layer 115, an I/O pad 117 and, in the embodiment illustrated, a plurality of electrodes 114 are present. The electrodes 114 are electrically connected to the transistor layer 112 via the interconnection layer 113. The I/O pad 117 is also electrically connected to the transistor layer 112 via the interconnection layer 113.

According to some embodiments, a first part of a first major surface of the microchip 103 may cover the fluidic substrate 101, a second part of the first major surface of the microchip 103 may not cover the fluidic substrate 101. In these embodiments, the microchip 103 may either be larger than the fluidic substrate 101, or it may be laterally shifted with respect to the fluidic substrate 101 so that a portion of the microchip 103 forms an overhang with respect to the fluidic substrate 101. The second part of the first major surface of the microchip 103 may comprise at least one I/O pad 117 to have access to the I/O pad 117.

Figure 22:
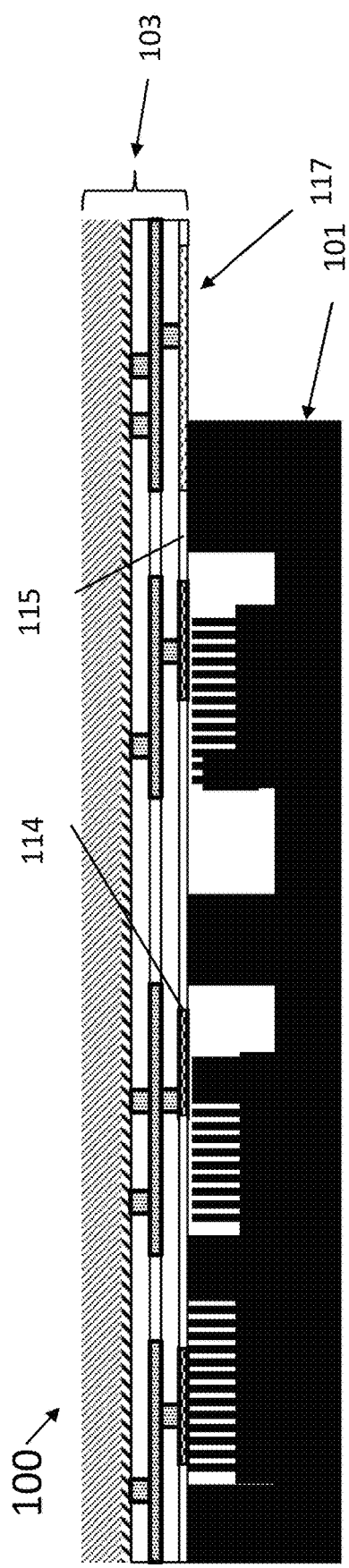
FIG. 22 schematically illustrates a microchip for use in a device, the microchip comprising an I/O pad bonded or clamped to a fluidic substrate, wherein a part of the microchip overlaps the fluidic substrate and a part forms an overhang with respect to the fluidic substrate, according to an example embodiment.

FIG. 22 illustrates a microchip 103 as illustrated in FIG. 21, bonded or clamped to a fluidic substrate 101. In this embodiment, a first part of the microchip 103 fully covers the fluidic substrate 101 wherein electrodes 114 are in direct contact with a fluid sample when present in the micro-fluidic component 102 of the device 100. The bonding layers 115 are used to bond a first part of the microchip 103 to the fluidic substrate 101. A second part of the microchip 103 forms an overhang which does not cover the fluidic substrate 101. The second part comprises the I/O pad 117. This overhang allows easy access to the I/O pad 117. This allows standard I/O pad dimensions and packaging approaches to be used for inserting the substrate in slots typically used for smartcards. This also means that additional processing steps to fabricate silicon I/O connections (e.g. a hole through the substrate and transistor layer) to access electrical signals in the microchip 103 are not required.

According to embodiments of the embodiment, when the lid 103 has smaller dimensions than the fluidic substrate 101, the surface of the lid 103 is in contact with or covers at least a part of the surface of the fluidic substrate 101, at least partially covering the micro-fluidic component 102.

According to some embodiments, the fluidic substrate 101 further may comprise at least one optical waveguide to allow optical excitation and sensing of the fluid sample when present in the device 100.

According to some embodiments, the fluidic substrate 101 and/or the lid 103 comprises at least one through-hole for application of a biochemical reagent to a region of the micro-fluidic component 102 or to a region of the lid 103. The through-holes in the fluidic substrate 101 and/or the lid 103 allow the application of biochemical reagents to specific regions of the micro-fluidic component 102 or to specific regions of the lid 103. This may allow reagents to be applied after attachment of the lid 103 to the fluidic substrate 101.

Figure 23:
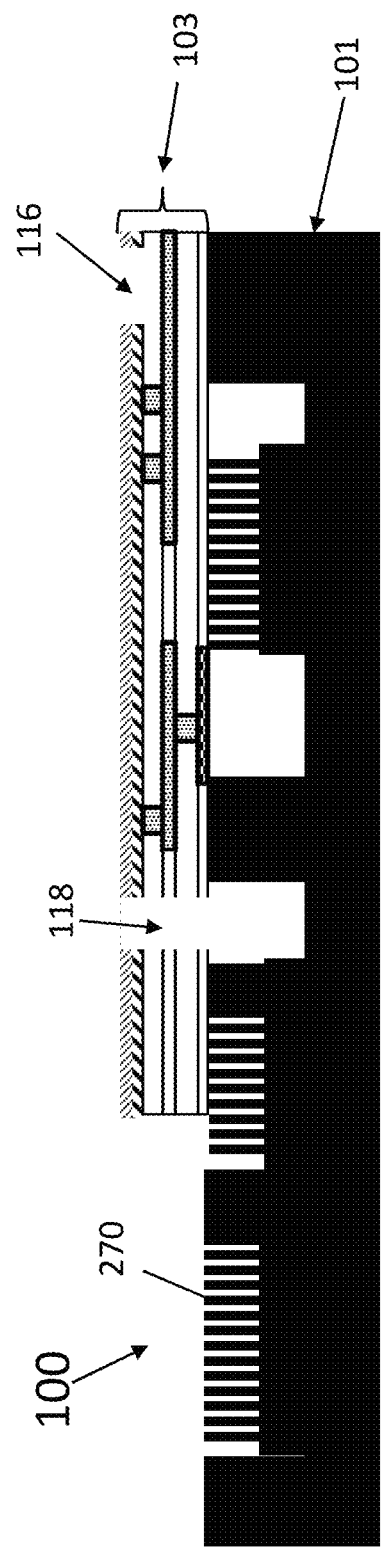
FIG. 23 schematically illustrates the bonding of a microchip with a fluidic substrate, wherein the microchip comprises a through hole, according to an example embodiment.

According to some embodiments, the microchip 103 may comprise at least one through-hole 118. When attached to the fluidic substrate 101, the through hole 118 in the microchip 103 allows reagent spotting on a specific location of the micro-fluidic component 102 in the fluidic substrate 101 or on a specific part of the microchip 103. FIG. 23 schematically illustrates a side view of a device, the device comprising a fluidic substrate 101, a microchip 103 attached thereon, whereby the microchip comprises at least one though-hole 118. The through-hole may be provided strategically, for example on an open area of the micro-fluidic component 102.

In this embodiment, the microchip further comprises a silicon I/O connection 116. As illustrated, the microchip 103 completely covers a part of the fluidic substrate 101.

Figure 24:
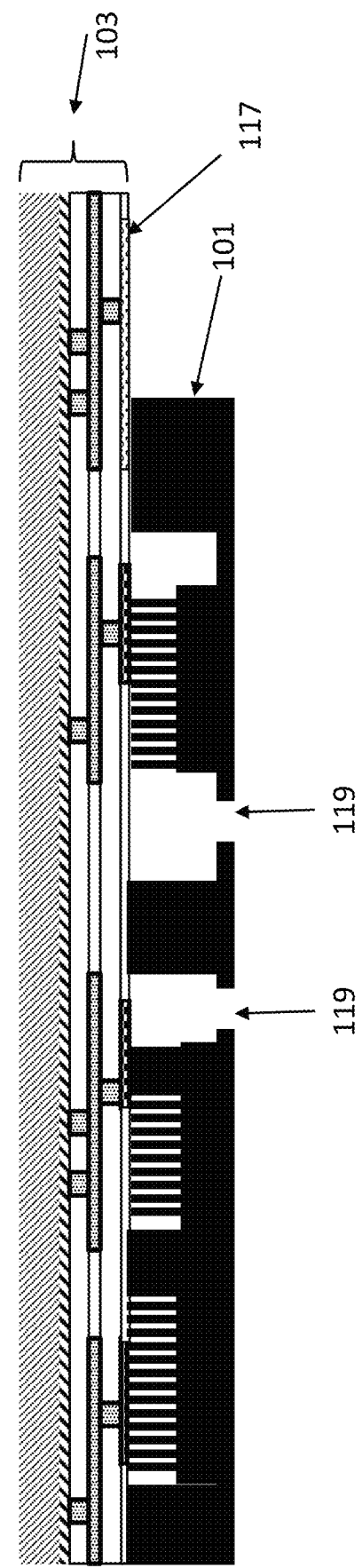
FIG. 24 schematically illustrates the bonding of a microchip with a fluidic substrate, wherein the fluidic substrate comprises two through holes, according to an example embodiment.

According to same or alternative embodiments, a first side of the fluidic substrate 101 comprises the open micro-fluidic component 102. The other side, opposite to the side where the micro-fluidic component 102 is provided, may comprise at least one through hole 119. The through hole 119 allows reagent spotting on a specific location of the micro-fluidic component 102 in the fluidic substrate 101 or on a specific part of the microchip 103. FIG. 24 illustrates such an embodiment wherein the fluidic substrate comprises two through holes 119. A part of the microchip 103 covers the fluidic substrate 101, the part not covering the fluidic substrate 101 but forming an overhang comprises an I/O pad 117.

According to some embodiments, the lid 103 may be bonded or clamped to the fluidic substrate 101 using a suitable bonding layer such as polymer, which may be a lithographically patterned polymer. The material for forming the bonding between the lid 103 and the fluidic substrate 101 is suitable for performing a glass-Si bonding, which may occur at a low temperature, for instance room temperature. This is compatible with electronic, e.g. CMOS, circuits being present on the lid 103 and which should not be destroyed by the bonding process, and with reagents being present on or in the fluidic substrate 101, and which should also not be destroyed by the bonding process. Suitable bonding materials for bonding the lid 103 to the fluidic substrate 101 are for instance photopatternable PDMS, obtainable from Dow Corning; SU8, obtainable from MicroChem; or OSTE, obtainable from Mercene Labs. These bonding materials all have room temperature as bonding temperature.

According to another embodiment, the lid 103 is bonded or clamped to fluidic substrate 101 using a semiconductor packaging technique. The use of semiconductor packaging techniques may be used when the fluidic substrate 101 is a glass substrate and the lid 103 is a microchip, e.g. a CMOS chip.

According to some embodiments, the device 100 may further comprise at least one metal contact electrically connected to the lid 103 for read-out of electrical signals from the lid 103. The at least one metal contact may be located on the lid 103, electrically connected to electronic circuitry in the lid 103. The position and shape of the metal contacts may be selected according to standards, allowing insertion of the device in standardized slots such as slots for memory cards (e.g. CompactFlash, SmartMedia, MultiMedia Card or Secure Digital (SD) memory cards) commonly used in communication devices such as mobile devices. The insertion of the device 100 in a mobile device allows processing of the electrical signals from the lid 103 by a processor and/or other electronic components present in the mobile device. For example, a processor of a smartphone may be used to process electrical signals and/or to display data.

According to some embodiments, at least a part of the lid 103 may be fabricated from a transparent material to allow optical inspection of a fluid sample when the fluid sample is present in the micro-fluidic component 102, even when no through-holes 118, 119 are provided in the lid 103 or fluidic substrate 101, respectively. The fluidic substrate may be transparent as it is fabricated from glass. The transparent material allows optical inspection of a fluid sample in the device 100. An optical detector may be used to optically inspect a fluid sample, in order for instance to detect an analyte. The optical detector may be an image sensor which may be part of an external device or may be integrated in the device 100. The transparent material may be a transparent oxide or polymer. For microscopy purposes, a part of the lid 103 may be transparent. For lens-free imaging purposes, a part of the lid 103 may be transparent to enable working in transmission mode wherein a radiation source may be used to radiate an object in a fluid sample in the device 100 through the transparent part of the lid 103 and a detector may be used to detect signals from the radiated object through the glass substrate 101. The signals may be diffraction patterns of a radiated object in the fluid sample.

Figure 33:
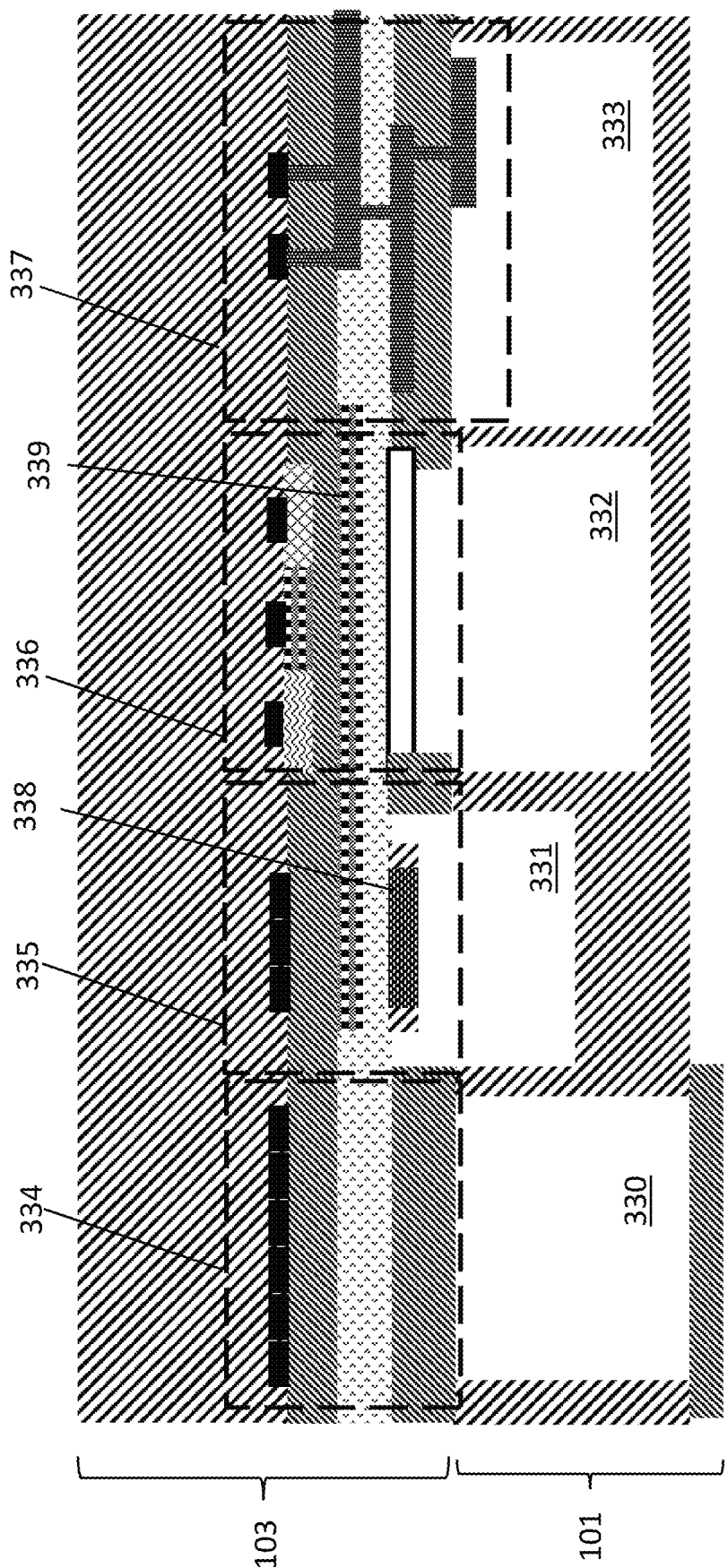
FIG. 33 is a schematic cross-sectional view of a device, wherein a plurality of functionalities are supported by a single semiconductor technology, according to an example embodiment.

FIG. 33 illustrates a device 100, where a fluidic substrate 101 and a lid 103 are bonded or clamped to one another, whereby the dimension of the lid and fluid substrate may be the same or different as described earlier. The fluidic substrate 101 may comprise different microfluidic components for multi-omic analysis, in the embodiment illustrated the device comprises a plurality of chambers 330, 331, 332, 333 and microfluidic channels (not illustrated). The chambers may have different depths, depending on their function and the type of measurement being performed. The chambers may be separated by valves that may be actuated in any suitable way, for instance by fluidic forces or by electricity. Electrodes for actuation may be provided on the fluidic substrate 101 or on the lid 103. The microchip forming the lid 103 may thus incorporate different functionalities, such as for instance a microscopic imager 334, e.g. a CMOS microscopic imager 334, optical detectors 335, 336, e.g. CMOS optical detectors 335, 336 and electrical circuitry 337, e.g. CMOS electrical circuitry 337, for heating and/or sensing. The microscopic imager 334 may comprise active pixels, e.g. CMOS active pixels, for readout of optical signals from the fluid sample in the microfluidic component 102. The optical detector 335 comprises an optical resonator 338. A waveguide 339 may be present for transporting measurement light from one location of the microchip 103 to another location. The waveguide may for instance be used for irradiating the sample for performing lens-free microscopy. Furthermore, filters may be provided in the fluidic substrate 101 or in the lid 103 for rejecting optical excitation from emission, so as to enable measurement of a fluorescent signal. Also multispectral filters may be provided in the fluidic substrate 101 or in the lid, for measurement fluorescent signals with multiple colors.

This way, detection of different types of markers can be performed within a single, possibly disposable, detection device.

According to some embodiments, a shape can be chosen for the device 100, whereby the shape of the device 100 allows insertion into a communication device, which may be a mobile communication device. According to some embodiments, the device 100 may have the shape/dimensions of a memory storage device, e.g. a memory card. The embodiments described herein allow for the dimensions of the device 100 to be adapted according to standards, e.g. according to standards of memory cards used in mobile devices such as: CompactFlash, SmartMedia, MultiMedia Card, Secure Digital memory cards or any other type. A device according to some embodiments may be made independent on the used communication device or present standards.

Figure 31:
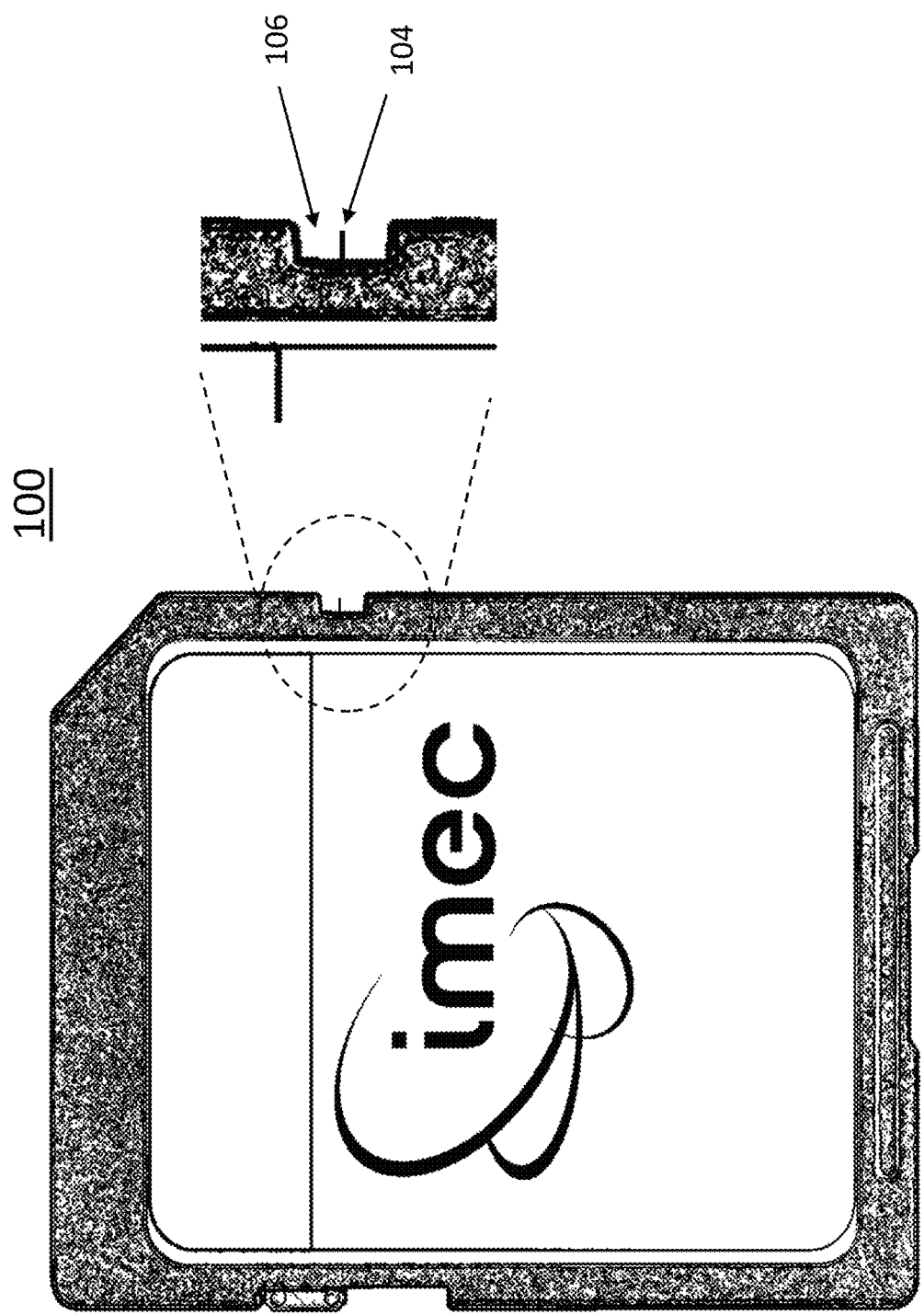
FIG. 31 illustrates a device in the shape of an SD card, according to an example embodiment.
Figure 32:
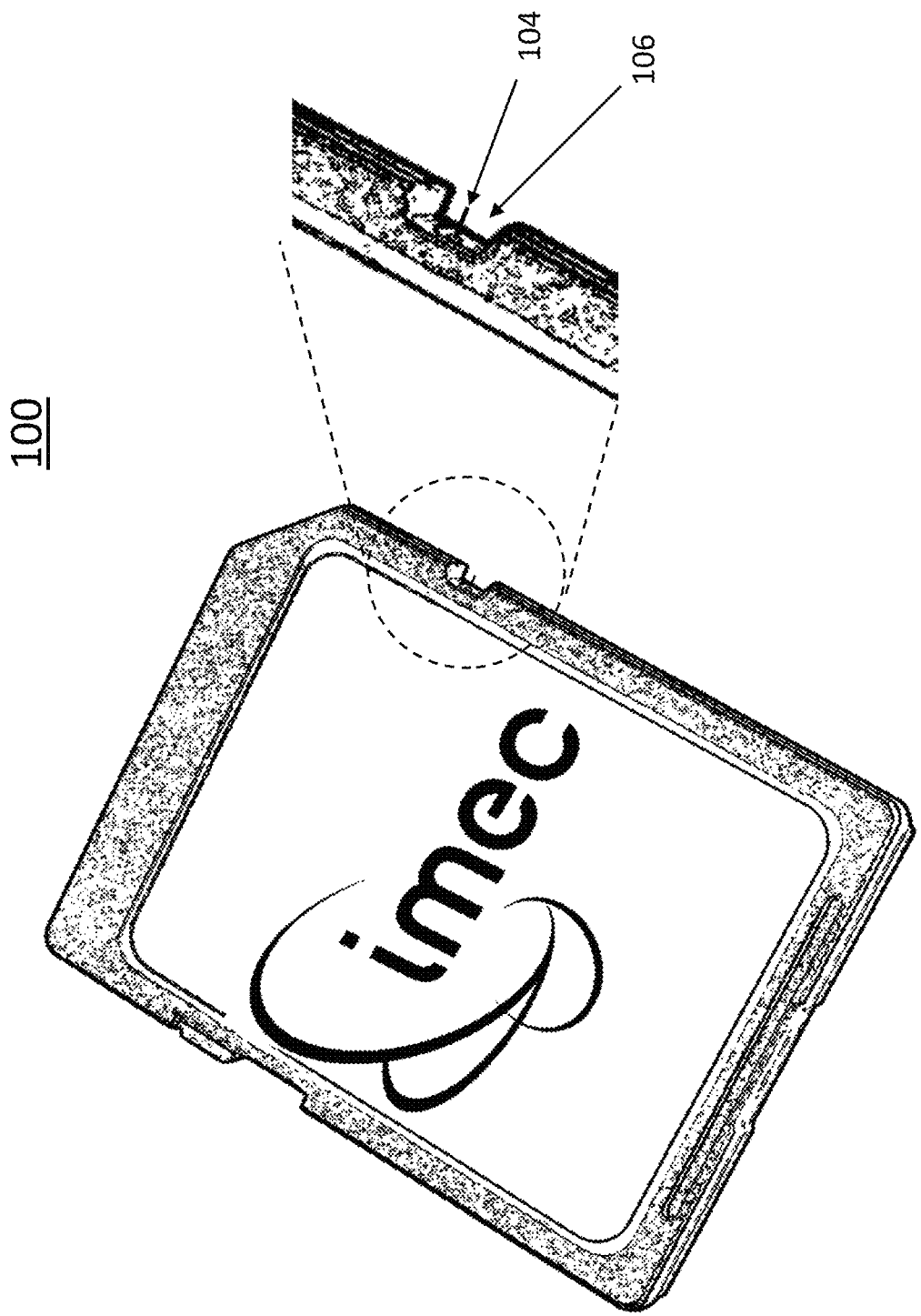
FIG. 32 illustrates a device the shape of an SD card, according to an example embodiment.

FIGS. 31 and 32 illustrate an embodiment wherein the device 100 has the shape of an SD card. Inside the cut-out 106 (which should be present according to SD card standards), a needle 104 is present. At the other side of the SD card, the metal contacts are present and electrically connected to the lid 103 to allow read-out of electrical signals from the lid 103 which may be further processed by the device in which the SD card is inserted.

According to some embodiments, the lid 103 or the fluidic substrate 101 may further comprise a compartment for powering the device 100, such as a battery compartment (not illustrated) which is electrically connected to the lid 103.

In a second aspect, some embodiments relate to a method of fabricating a device. The method according to some embodiments can for example be used to fabricate a device 100 as disclosed in the first aspect of the present disclosure. The method comprises: providing a fluidic substrate 101; providing a lid 103; attaching the fluidic substrate 101 to the lid 103 to close or cover the fluidic substrate 101 at least partly; characterized in that: the fluidic substrate 101 is a glass fluidic substrate and the lid 103 is microchip. The fluidic substrate 101 may be attached to the lid 103 using a semiconductor bonding process.

The fluidic substrate 101 is attached, for example bonded, to the lid 103 using a semiconductor bonding process, which may include low temperature/voltage bonding techniques. In conventional devices, bonding is performed using high temperature/voltage bonding techniques. These bonding techniques may damage electronic circuitry present in the microchip and/or reagents present in the microfluidic substrate 101. The use of a semiconductor bonding process enables bonding at lower temperatures/voltages and therefore preserves the electronic circuitry of the lid 103 and the reagents present in the microfluidic substrate 101. According to some embodiments, the bonding may be performed via a wafer to wafer or die to wafer bonding process such as direct glass to oxide bonding or bonding via a pattern-able polymer. Additionally, it may be advantageous to be able to perform the bonding at a low temperature in case some reagents are already spotted on one of the substrates during the fabrication flow. Alternatively, in some embodiments the lid 103 may be clamped to the fluidic substrate 101 such that at least a part of a micro-fluidic component in the fluidic substrate 101 is fluid-tightly closed.

The glass fluidic substrate 101 may for example be fabricated using a combination of coarse and fine structures in a single piece of glass substrate. The fine and coarse structures may be comprised in the micro-fluidic component. The coarse and fine structures are enabled by a combination of two hard masks, protection and de-protection of layers, and etching of the coarse and etching of fine structures.

Fine structures may be structures configured to e.g. enable a controlled capillary suction in the micro-fluidic component 102 of the device 100. The fine structures may for example comprise micro-pillars 270 and/or other microstructures. In some embodiments, the fine structures may be provided at regular or irregular distances in function of the desired functionality of the envisioned device. Fine structures may for example comprise microchannels as well. Coarse structures may for example be structures for storing larger volumes of fluids e.g. reagent storage 102b for storing reagents or a wick 102i.

The provided fine structures, like for example the glass micro-pillars 270 typically have lateral dimensions from 1 µm to 20 µm with aspect ratios between 20 to 50. High aspect ratios allow for having a high surface to volume ratio, essential for capillary flow and for enabling a gradient in the fluid sample. The high aspect ratio fine structures, combined with the coarse structures, allow to implement more complex capillary fluidic functions in a more compact footprint than is achievable with any other material. More complex functions include separation (e.g. cells from molecules), mixing, valving, and thermally controlled reactions. Moreover, glass is an inert material, which assists with towards implementation of biochemical reactions. One advantage of the compact fully integrated disposable device results from the advanced use of glass for the fluidic substrate and the lid comprising the microchip. The reduced footprint also results in reduced cost of the entire device.

According to some embodiments, the method comprises providing a fluidic substrate 101. According to embodiments providing a fluidic substrate 101 comprises providing a glass substrate 201, as schematically illustrated in FIG. 11, and patterning the glass substrate 201 to form fine structures like for example a micro-fluidic component 102 and a means for providing a fluid sample in the device 100, the micro-fluidic component 102 being configured to propagate a fluid sample via capillary force or via a force created by a vacuum compartment through the device 100.

According to some embodiments, as illustrated in FIG. 12 providing a fluidic substrate 101 comprises: providing a glass substrate 201, providing a mask 202, patterning the mask 202 by using a first patternable mask layer 210, so as to create fine structures 203 in the mask 202 (as illustrated schematically in FIG. 12); After the fine structures 203 in the first mask 202 are manufactured, a first protection layer 204 is provided so as to protect the patterned mask 202; After the patterned mask 202 is protected, a second patternable mask layer 211 (as illustrated schematically in FIG. 13) is provided on the first protection layer 204 and coarse structures 205 are created in the second patternable mask layer 211; in some embodiments the course structures are not provided on top of the protected fine structures 203. In a next step the coarse structures 205 are etched in the glass substrate 201 through the patterned second mask layer 211 (as illustrated schematically in FIG. 14); in a next step the second patterned mask layer 211 is removed and a second protection layer 206 is grown (as illustrated schematically in FIG. 15) for protecting the etched coarse structures 205, wherein the first protection layer 204 on the fine structures 203 prevents growth of the second protection layer; then the first protection layer 204 (as illustrated in FIG. 16) is removed and the fine structures 203 are etched in the glass substrate 201 using the second protection layer 206 as an etch mask; in a final step the second protection layer 206 is removed (as illustrated schematically in FIG. 17).

The resulting structure is a glass microfluidic substrate 101 comprising fine and coarse structures, which may be used in a device according to an example embodiment.

In a specific embodiment, a glass substrate 201 is provided. A first mask 202, e.g. a mask comprising SiC or SiN is provided on top of the glass substrate 201. Thereafter, on top of the first mask 202, a photoresist layer 210 is deposited, e.g. a polymer resist. Thereafter, the photoresist layer 210 is then patterned (as illustrated in FIG. 11). Thereafter, the photoresist layer 210 is etched to create the fine structures 203 in the first mask 202. Thereafter, the photoresist layer 210 is removed. Thereafter, the fine structures 203 including the first mask 202 are covered with a first protection layer 204, e.g. an oxide or a metal layer (as illustrated in FIG. 12). Thereafter, a second mask 211, e.g. a mask comprising SiC or SiN, is deposited on the first protection layer 204. Thereafter the second mask 211 is patterned (as illustrated in FIG. 13). Thereafter, an etching is performed to remove the parts of the first protection layer 204 and the first mask 202 which are not located underneath the second mask 211 and partly remove material from the glass substrate 201 to create the coarse structures 205 (as illustrated in FIG. 14). Thereafter, the remaining material of the second mask 211 is completely removed. Thereafter a second protection layer 206 is formed to protect the glass substrate (FIG. 15) such that afterwards the first protection layer 204 can be completely removed (FIG. 16). In a final step, the second protection layer 206 may be removed (FIG. 17). The final product is a glass substrate having fine and coarse structures, whereby the fine structures have a high aspect ratio.

The etching may be performed using processing steps suitable for etching glass substrates which are known to a person skilled in the art. Etching steps may comprise dry (e.g. DRIE or plasma etching) and/or wet etching (e.g. HF etching) process steps.

FIGS. 11-17 illustrate how a glass fluidic substrate may be fabricated and more specifically how a glass fluidic substrate 101 may be fabricated. According to some embodiments, the fluidic substrate 101 may be fabricated by provided a glass substrate 201 and performing following steps:

Patterning fine structures 203, the patterning fine structures 203 comprising, providing an mask 202 on the glass substrate 201, patterning the mask 202 to create fine structures 203 in the mask 202;

providing a first protection layer 204 to protect the patterned mask 202;

performing lithography of coarse structures 205, whereby the coarse structures 205 are not provided on the fine structures 203;

performing etching of the coarse structures 205, such that coarse structures 205 are etched in the glass substrate 101;

growing a second protection layer 206 for protecting the coarse structures 205 wherein the first protection layer 204 on the fine structures 203 prevents growth of the second protection layer;

removing the first protection layer 204 and etch the fine structures 203 in the glass substrate 101;

removing the second protection layer 206.

According to some embodiments, the first protection layer 204 may be a nitride layer.

According to some embodiments, providing a microchip 103 comprises: providing a glass substrate 111, fabricating a transistor layer 112 atop the glass substrate and providing an interconnection layer 113 atop the transistor layer. The interconnection layer may comprise at least one metal layer.

The microchip 103 is may be fabricated using standard semiconductor process techniques, e.g. standard CMOS processing techniques.

Further, on top of standard semiconductor process flows, additional components may be deposited or patterned on the interconnection layer 113 such as biocompatible electrodes, a bonding layer, I/O pads or other components.

According to some embodiments, through holes 119, 118 may be etched through the fluidic substrate 101 or the microchip 103 to enable fluidic access for applying of reagents to the fluidic substrate 101 or to the microchip 103. The through-holes in the microchip 103 may be fabricated whilst fabricating silicon I/O interconnections 116 in the microchip 103. The through-holes in the fluidic substrate 101 may be fabricated by first thinning the fluidic substrate 101 and then etching the through-holes.

According to some embodiments, the microchip 103 may be bonded to the fluidic substrate 101 using a die to wafer or wafer to wafer bonding process.

To access electrical signals of the microchip 103, silicon I/O contacts 116 may be provided. According to some embodiments, the contacts may be fabricated by thinning the glass substrate 111 of the microchip 103 and performing a back side etching on the glass substrate 111 to gain access to a metal layer of the interconnection layer 113.

Alternatively, a microchip 103 comprising an I/O pad 117 at a first side of the chip 103 may be provided, wherein the first side of the microchip 103 is bonded or clamped to the fluidic substrate 101 and wherein the first side of the microchip 103 comprising the I/O pad 117 does not cover the fluidic substrate 101. This is for example illustrated in FIG. 22. The I/O pad 117 is accessible when the microchip 103 is bonded or clamped to the fluidic substrate 101. The I/O pad 117 may be used as a metal contact on a memory card.

According to some embodiments, the microchip 103 may be bonded or clamped to the fluidic substrate 101 while aligning at least one electrical component on a first side of a microchip 103 with the micro-fluidic component 102. For example, sensing and actuating electrodes on the first side of the microchip 103 are aligned with a sensing or actuation side in the fluidic substrate 101. This allows direct contact of a fluid sample with electrical components present on the microchip 103 when a fluid sample is present in the device 100.

According to some embodiments, surfaces of the fluidic substrate 101 and the lid 103 are partially or fully coated to modify surface interactions with the fluid sample. The surfaces may be inner surfaces of the micro-fluidic component 102 or a surface of the microchip 103 that is bonded or clamped to the fluidic substrate 101. In particular those parts of the surface of the microchip 103 that are in contact with a fluid sample present in the micro-fluidic component 102. The coating may be a hydrophilic coating.

According to some embodiments, the surfaces of the micro-fluidic component 102 and/or the side of the microchip 103 bonded or clamped to the fluidic substrate 101 can be made hydrophilic in order to improve the wetting behavior of the surfaces, thereby promoting e.g. capillary flow. The surfaces can also be treated in order to avoid absorption or adhesion of biomolecules on the walls. The coating can be done for example by vapor coating with silanes. According to some embodiments, the coating may be performed locally on certain parts of the fluidic substrate 101 (e.g. in some micro-fluidic channels) or on certain parts of the microchip 103.

Some embodiments may improve the functionality, portability and manufacturability of compact disposable point of care devices.

A particular embodiment of the present disclosure is a fully integrated device with a needle or an inlet for the intake of blood or any other body fluid. The device features a fluidic system for the propagation of a fluid sample through the device. Optionally a capillary pump functioning as the wicking zone of the capillary fluidic system may be used to propagate the fluid sample in the device. Alternatively a force created by opening a vacuum compartment or removing a vacuum seal or element present in the fluidic substrate may be used to propagate the fluid sample in the device. A lid comprising a sensor chip adapted to read out signals produced by biochemical sensing reactions inside the fluidic system may be used to add biosensing functionality to the device. Further, the device features a data communication interface for sending data to a personal computer, a computing unit, smartphone or any other wireless communication device. The device may function as a stand-alone system wherein a power interface such as a battery powers electronic circuitry such as a micro-chip in the device. Alternatively, the device may be powered via a communication port of the device.

A device according to some embodiments may further comprise fluidic manipulation structures including filtering, mixing, valves structures. A protection structure with a cut off zone to protect and prevent breaking the needle before usage may be present to avoiding contamination before usage. Structures such as electrically controllable fluidic manipulation structures including electrowetting, electro and dielectrophoretic manipulation may be present to interact with a fluid sample in the device. Electronic controllable heaters may be present for accurately controlling the temperature of the chip or for thermal cycling purposes.

Another example embodiment includes an elegant, low cost and compact manner to fabricate all of the above functions by providing a substrate which may comprise lithographically defined fine structures, like for example channels, micro pillars and microstructures of various shapes fabricated by deep Reactive Ion Etching and designed to function as a fluidic platform. The glass fluidic substrate according to some embodiments may have a provision for making a needle and a cut off zone for protecting the needle. The glass fluidic substrate may have different etch depths allowing for precise control over the volume and capillary flow of a fluid sample in the device.

The glass fluidic substrate may be at least partially closed by a lid, for example a CMOS substrate comprising CMOS electronics comprising a transistor layer. The electronics may be designed to provide functionality including sensing, actuating, signaling, data processing and data communication and therefore replaces the point of care instrument. Some of the electrodes may be in direct contact with the fluid, these electrodes may be protected in a fluid compatible manner. The substrate may be closed by the CMOS substrate by bonding both substrates in a leakage free and biocompatible manner. This can be done via a wafer to wafer or die to wafer bonding process such as bonding via a patternable polymer. The inner substrate surfaces which may be in contact with the body fluids may feature a hydrophilic layer via coating of the inner channels. Additionally, through wafer holes may be fabricated in the fluidic substrate for supplying reagents after the device has been bonded or clamped. For each analysis, different reagents can be supplied. The same device becomes configurable for different diseases by simply adding reagents through the through-holes in the last production step. The device may be manufactured using mass production processing steps which lower production cost and enable the device to be used as disposable device.

Further, the device may comprise components to enable interfacing with standard user interfaces.

For example, the use of such a device as a smartcard in wireless communication devices inserted in slots typically foreseen for smartcards. For example, the use of such a device together with a compact and cheap battery and low cost communication device (e.g. Bluetooth, NFC). For example, the use of such a device together with a wired communication interface (e.g. USB).

Some embodiments may be used to detect DNA/RNA from body fluids and perform an analysis to detect: mutations (ancestry, drug dosing, disease predisposition), miRNA (marker for cancer and other diseases), pathogen DNA/RNA (infectious diseases such as HepC, HIV, etc.), microbiome DNA. Further, the device may be used to detect proteins such as biomarkers for a specific disease (cancer, Alzheimer's, infectious diseases, heart disease, cancer etc.) Further, the device may be used to detect small molecules and metabolites to reveal metabolic information (cholesterol). Further, the device may be used to detect biomarkers from exosomes. Further the device may be used to perform microscopy to perform a blood count, analyze cells present in the blood (e.g. circulating tumor cells), identify infectious agents (e.g. malaria) and to detect blood disorders (e.g. sickle cell anemia). According to a further aspect of the disclosure, the device as presented in the first aspect of the disclosure may be comprised in a package. The device may be integrated, encapsulated or embedded at least partly in the package. The package may be fabricated from plastic. The package may be fabricated from a shock-resistant, resilient material.

According to some embodiments, the package may comprise an inlet 260 for supplying a fluid sample to the micro-fluidic component.

According to some embodiments, a fluidic compartment is attached to the device 100. The fluidic compartment can be fluidically connected to the micro-fluidic component of the fluidic substrate by opening the fluidic compartment. When the fluidic compartment is not a part of or embedded in the fluidic substrate, the size of the fluidic substrate may be reduced thereby contributing to a reduced cost of the device. The fluidic compartment may be a sealed fluidic compartment for storing a liquid which may be opened during device operation. The liquid may be a reagentia or a washing solution. The fluidic compartment may be adapted to open and release its contents to the micro-fluidic component when triggered by an electrical signal, e.g. generated by the microchip or generated by the fluidic substrate, e.g. from a fluidic sensor present in the fluidic substrate or in the package.

According to some embodiments, the device may comprise a fluidic structure configured to perform rudimentary pre-processing (sample prep) on a fluid sample before supplying the prepped fluid sample to the micro-fluidic component of the fluidic substrate. The fluidic structure may be separate from the fluidic substrate. The fluidic substrate may be smaller thereby contributing to reduced cost of the device.

According to some embodiments, the device may comprise electronic circuitry that is electrically connected to the microchip of the device. This electronic circuitry may be present on a PCB. The electronic circuitry may be configured to wirelessly transmit data and/or to process data coming from the microchip. By doing so, the processing performed on the micro-chip can be relaxed to reduce heat generated by that micro-chip. Such heat is disadvantageous as it may destroy biological material present in the device. The electronic circuitry may be fabricated using a different, cheaper semiconductor technology than the semiconductor technology of the micro-chip. This contributes to a further reduction of the total cost of the device.

According to some embodiments, at least a part of the package may be fabricated from a transparent material, e.g. glass or a transparent polymer, for inspecting the fluidic substrate. Because the fluidic substrate is fabricated from glass, a fluid sample inside the fluidic substrate may be inspected using an external optical tool, via the transparent part of the package.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

The invention claimed is:

1. A device comprising:
  a fluidic substrate comprising:
    a micro-fluidic component comprising a micro-fluidic compartment embedded in the fluidic substrate comprising fine structures and coarse structures etched therein, wherein the fine structures comprise an aspect ratio of at least 20, and wherein the fine structures comprise a plurality of micro-pillars configured to propagate a fluid sample;
    a needle or an inlet for providing the fluid sample connected to the micro-fluidic component; and
    one or more filters configured to reject optical excitation from an emission generated by the fluid sample in response to the optical excitation; and
  a lid attached to the fluidic substrate thereby at least partly covering the fluidic substrate and at least partly closing the micro-fluidic component, wherein the fluidic substrate is a glass fluidic substrate, wherein the lid is a microchip, and wherein the lid comprises at least one optical waveguide to allow optical excitation and sensing of the fluid sample when present in the device.

2. The device according to claim 1, wherein the fluidic substrate is configured to propagate the fluid sample through the micro-fluidic component via capillary force.

3. The device according to claim 1, wherein the fluidic substrate comprises a vacuum compartment connectable to the micro-fluidic component and the vacuum compartment is adapted for creating a suction force in the micro-fluidic component when the vacuum compartment which is connected to the micro-fluidic component is opened, thereby propagating the fluid sample through the micro-fluidic component.

4. The device according to claim 1, wherein at least a part of the lid is in direct contact with the fluid sample when the fluid sample is present in the device.

5. The device according to claim 1, wherein the lid comprises a transistor layer, the transistor layer being electrically connected to at least one electrical component present in the lid, the electrical component being at least one of the following:
  biosensing circuitry, biosensing circuitry for fluorescent detection, biosensing circuitry for lens-free detection of particles, electrodes for sensing purposes, electrodes for fluid manipulation purposes, circuitry for data communication purposes, circuitry for wireless data communication purposes, temperature sensors, heater electrodes for temperature control and fluid sensors and electrodes for fluidic viscosity control.

6. The device according to claim 1, wherein the needle is integrated with the fluidic substrate, the needle being fabricated from glass and comprising an inner fluidic channel connected to the micro-fluidic component and wherein the needle is a protruding portion of a horizontal plane of the fluidic substrate and positioned to penetrate skin tissue when pressed against the skin tissue, wherein the fluidic substrate and the needle are fabricated from a single piece of glass.

7. The device according to claim 1, wherein the fluidic substrate or the lid comprises at least one through-hole for application of a biochemical reagent to at least one region of the micro-fluidic component or to at least one region of the lid.

8. The device according to claim 1, wherein the lid is bonded to the fluidic substrate using a lithographically patterned polymer.

9. The device according to claim 1, further comprising metal contacts electrically connected to the lid for read-out of electrical signals from the lid.

10. The device according to claim 1, wherein at least part of the fluidic substrate or the lid is fabricated from a transparent material to allow optical inspection of the fluid sample when the fluid sample is present in the micro-fluidic component.

11. A method for fabricating the device of claim 1 for analyzing a fluid sample, the method comprising:
  providing the fluidic substrate;
  providing the lid; and
  attaching the lid to the fluidic substrate to close the fluidic substrate at least partly, wherein the fluidic substrate is the glass fluidic substrate and the lid is the microchip.

12. The method according to claim 11 wherein providing a fluidic substrate comprises:
  providing a glass substrate, providing a mask on the glass substrate, patterning the mask to create fine structures in the mask;
  providing a first protection layer to protect the patterned mask;
  patterning coarse structures in a second patternable mask;
  etching of the coarse structures in the glass substrate through the second patterned mask;
  growing a second protection layer for protecting the etched coarse structures;
  removing the first protection layer and etching the fine structures using the second protection layer as an etch mask; and
  removing the second protection layer.

13. The method according to claim 11, wherein surfaces of the fluidic substrate and the lid are partially or fully coated to modify surface interactions of the fluidic substrate with the fluid sample.

14. The method according claim 11, for fabricating a device for analyzing a fluid sample, the device comprising:
  a fluidic substrate comprising a micro-fluidic component embedded in the fluidic substrate configured to propagate a fluid sample, and a needle or inlet for providing a fluid sample connected to the micro-fluidic component; and
  a lid attached to the fluidic substrate thereby at least partly covering the fluidic substrate and at least partly closing the micro-fluidic component, wherein the fluidic substrate is a glass fluidic substrate and wherein the lid is a microchip.

15. A packaged device, comprising a package encapsulating a device for analyzing a fluid sample, the device comprising:
  a fluidic substrate comprising a micro-fluidic component embedded in the fluidic substrate comprising fine structures and coarse structures etched therein, wherein the fine structures comprise an aspect ratio of at least 20, and wherein the fine structures comprise a plurality of micro-pillars configured to propagate a fluid sample;
  a needle or inlet for providing a fluid sample connected to the micro-fluidic component;
  one or more filters configured to reject optical excitation from an emission generated by the fluid sample in response to the optical excitation; and
  a lid attached to the fluidic substrate thereby at least partly covering the fluidic substrate and at least partly closing the micro-fluidic component, wherein the fluidic substrate is a glass fluidic substrate, wherein the lid is a microchip, and wherein the lid comprises at least one optical waveguide to allow optical excitation and sensing of the fluid sample when present in the device.

16. The packaged device according to claim 15, further comprising a sealed fluidic compartment adapted to be fluidically connected to the micro-fluidic component, when opened.

17. The packaged device according to claim 15, further comprising electronic circuitry electrically connected to the microchip of the device.

18. The device according to claim 1, wherein the lid further comprises a radiation source coupled to the at least one optical waveguide and configured to generate the excitation.

19. The device according to claim 1, wherein the at least one optical waveguide is further configured to receive an emission generated by the fluid sample in response to the optical excitation, and wherein the at least one optical waveguide further comprises a detector coupled to the at least one optical waveguide and configured to receive the emission and to generate an image based on the emission.

20. The device according to claim 1, wherein the one or more filters or the lid comprises a multispectral filter.

* * * * *